United States Patent
Gulbins et al.

(10) Patent No.: US 10,688,065 B2
(45) Date of Patent: Jun. 23, 2020

(54) SPHINGOID COMPOUNDS FOR PROPHYLAXIS AND/OR THERAPY OF A VIRAL INFECTION

(71) Applicant: Harbins Ruhr Bioscience, Inc., Wilson, WY (US)

(72) Inventors: Erich Gulbins, Essen (DE); Karl Sebastian Lang, Essen (DE); Judith Bezgovsek, Essen (DE)

(73) Assignee: Harbins Ruhr Bioscience, Inc., Wilson, WY (US)

( * ) Notice: Subject to any disclaimer, the term of this patent is extended or adjusted under 35 U.S.C. 154(b) by 0 days.

(21) Appl. No.: 16/588,361

(22) Filed: Sep. 30, 2019

(65) Prior Publication Data

US 2020/0113850 A1 Apr. 16, 2020

(30) Foreign Application Priority Data

Oct. 10, 2018 (DE) .......................... 10 2018 217 334

(51) Int. Cl.
*A61K 31/131* (2006.01)
*A61P 31/16* (2006.01)
*A61K 9/00* (2006.01)

(52) U.S. Cl.
CPC .......... *A61K 31/131* (2013.01); *A61K 9/0019* (2013.01); *A61P 31/16* (2018.01); *A61K 9/0043* (2013.01); *C12Y 305/01023* (2013.01); *C12Y 305/01109* (2013.01)

(58) Field of Classification Search
CPC .. A61K 31/131; A61K 9/0019; A61K 9/0043; A61P 31/16
USPC ....................................................... 514/625
See application file for complete search history.

(56) References Cited

U.S. PATENT DOCUMENTS

| 9,012,396 B2 | 4/2015 | Yedgar |
| 2008/0090913 A1 | 4/2008 | Braxmeier et al. |
| 2015/0126564 A1 | 5/2015 | Hahm et al. |
| 2016/0113954 A1 | 4/2016 | Fathi et al. |

FOREIGN PATENT DOCUMENTS

| DE | 3819870 A1 | 12/1988 | |
| WO | 2004017949 A2 | 3/2004 | |
| WO | 2006059897 A1 | 6/2006 | |
| WO | WO-2012100835 A1 * | 8/2012 | ........... A61K 31/164 |
| WO | 2014061016 A1 | 4/2014 | |

OTHER PUBLICATIONS

Machesky et al Journal of Biological Chemistry, 2008, 283(38) 26148-26160 (Year: 2008).*
Turner, Nigel et al.; Nature Communications; vol. 9, No. 3165; 2018; DOI: 10.1038/s41467-018-05613-7.
Schiffman, S.; Biochimie; Feb. 2012;94(2):558-65. doi: 10.1016/j.biochi.2011.09.007.

* cited by examiner

*Primary Examiner* — Yevgeny Valenrod
(74) *Attorney, Agent, or Firm* — Dinsmore & Shohl LLP; Weston R. Gould

(57) ABSTRACT

Provided are processes for the prevention or treatment of viral infection in a subject. Some aspects provide administration of a sphingoid compound, optionally sphingosine, an active ingredient that activates generation of a sphingoid base, optionally of sphingosine; or an active agent that inhibits the degradation of a sphingoid base, optionally of sphingosine, to a subject such as a human. By increasing the local concentration of sphingosine in a subject or an area of a subject to which the composition is administered such as the nose or interior of the nose or portion thereof, the ability of viruses to infect the subject or cells thereof is reduced thereby treating of preventing infection by the virus.

3 Claims, 18 Drawing Sheets

SPHINGOID COMPOUNDS FOR PROPHYLAXIS AND/OR THERAPY OF A VIRAL INFECTION

CROSS REFERENCE TO RELATED APPLICATIONS

This application depends from and claims priority to German Patent Application No: 102018217334.6 filed on Oct. 10, 2018, the entire contents of which are incorporated herein by reference.

FIELD

This disclosure relates generally to treatments or prophylactics for viral infection in an organism.

BACKGROUND

Viral infections are the result of passive or active penetration of a virus and/or viral genome (ribonucleic acid or deoxyribonucleic acid) into a cell of an organism. Viral infection may also lead to subsequent propagation of the virus within the organism. The process of viral penetration into a cell requires overcoming the cell membrane typically. Some viral infection occurs by an endocytotic mechanism whereby an invagination of the cell membrane is created to form a vesicle (endosome) resulting in the passive uptake of the virus into the cell. Within the cell, the virus escapes from the endosome by fusion of the outer viral membrane with the membrane of the endosome. Alternatively, the virus actively injects the viral genome into the cytoplasm of the cell without itself entering into the cell. Both mechanisms ultimately lead to the entry of viral genome into the cytoplasm of the cell.

Viral penetration into the cell is usually followed by a propagation of the virus within the cell and subsequent release of the propagated virus from the cell. The released virus is subsequently capable of infecting further cells. A viral infection may be followed by a viral infectious disease, which manifests itself in terms of symptoms based on the viral infection.

Many attempts have been made to address viral infections by targeting particular components of the viral life cycle. Drugs that target viral replication within the cell represent a key inhibitory target mechanism in the field. Alternatively, some attempts have been made to target the mechanisms by which viruses enter a cell. For example, WO 2004/017949 attempts to prevent viral entry into a cell by disrupting ceramide-rich lipid rafts on the surface of cells. The reference attempts to use inhibitors of acid sphingomyelinase and/or inhibitors of ceramide or phosphorylcholine, products of the reaction catalyzed by this enzyme to alter the presence and characteristic of lipid rafts on the membrane surface.

Each of the viral targeting mechanisms of the past suffer significant drawbacks such as viral mutation leading to escape and reduced effectiveness of compositions, unwanted systematic or other side effects, the ability to target only a single virus type, or low success. As such, new compositions and mechanisms are needed for prophylaxis or treatment of viral infection.

SUMMARY

This disclosure provides new compositions and methods for the prophylaxis or treatment of viral infection in a subject. The compositions may be used to target infection by a single virus type, illustratively rhinovirus, but may also have broad spectrum functionality and ability to prevent or reduce infection by a wide array of viruses. As such, provided are sphingoid compositions for use in the prophylaxis and/or therapy of a viral infection. The compounds and methods herein provide simple and efficient prophylaxis and/or therapy for viral infections and/or viral infectious diseases. Also provided is a medicament or a pharmaceutical composition, a food or food supplement, a feed or feed supplement and a plant protection agent. The compounds and methods provided herein may be used for the inhibition of bacteriophages, for the stabilization and/or spreading of a bacterial flora and for the avoidance of the formation of resistant bacterial strains.

BRIEF DESCRIPTION OF THE DRAWINGS

The aspects set forth in the drawings are illustrative and exemplary in nature and not intended to limit the subject matter defined by the claims. The following detailed description of the illustrative aspects can be understood when read in conjunction with the following drawings.

DETAILED DISCLOSURE

Figure 1:
FIG. 1 illustrates a schematic of the natural metabolism of sphingomyelin (SM) illustrating the synthesis and breakdown of sphingosine (SPH).

Provided in this disclosure are compounds and methods for the treatment or prophylaxis of viral infection in a subject such as a mammal. On the basis of cell and animal experiments, the inventors were able to demonstrate that, sphingoid compounds, such as sphingosine, and/or active ingredients which influence the degradation and/or the generation of a sphingoid compound, optionally of sphingosine, in vivo, such as ceramidase agonists and/or sphingosine kinase inhibitors, can be used for a prophylaxis and/or therapy of viral infections and/or viral infectious diseases. For instance, the inventors were able to show in particular that it is possible to prevent a viral infection by means of an increase in the in vivo concentration of sphingosine or to successfully control a viral infection that has already occurred and/or a viral infectious disease which is already manifested by means of an increase in the in vivo concentration of sphingosine. Furthermore, the inventors were able to show that a viral infection and/or viral infectious disease is prevented by an increased in vivo concentration of sphingosine. As such, provided are robust, rapid, and efficient methods of preventing or reducing viral infection of a subject and/or to the cells of a subject.

Processes as provided herein according to some aspects include administering to a subject a sphingoid compound, optionally a sphingoid base, prior to, concomitant with, or following the subject being contacted by a virus.

As used herein, a "subject" is a human, a non-human animal, such as, for example: a non-human mammal optionally a horse, cow, pig, dog, or cat; a bird optionally a chicken, turkey, goose, or other; a fish; a reptile; an amphibian; a mollusc; an insect or a spider; a cell; or a plant.

As used in this disclosure, the term "sphingoid base" can mean a single type of sphingoid base (singular) or a plurality of different, i.e. two or more different, sphingoid bases, optionally a mixture of different sphingoid bases. A sphingoid base includes salts thereof and/or hydrates thereof and/or solvates thereof and/or polymorphs thereof and/or optical isomers, optionally enantiomers and/or diastereomers and/or epimers, thereof and/or mixtures thereof.

As used in this disclosure, the term "active ingredient" can mean a single type of active ingredient (singular) or a plurality of different, i.e. two or more different, active ingredients, optionally a mixture of different active ingredients.

As used in this disclosure, the term "prophylaxis" is to be understood to mean a preventive measure suitable for preventing a viral infection and/or viral infectious disease. The preventive measure can optionally be administering a sphingoid based as provided herein to a subject prior to exposure to a virus or reexposure to a virus. Optionally, the preventative measure is a vaccination, and this will be discussed in detail below.

As used in this disclosure, the term "therapy" is to be understood to mean the treatment of a viral infection and/or viral infectious disease. The treatment can be either a causal treatment (so-called causal therapy), i.e. a treatment aiming at the elimination of the cause of the disease, or a symptomatic treatment (so-called symptomatic therapy), i.e. a treatment aiming at the elimination of symptoms. Therapy may be amelioration of one or more symptoms of a viral infection or viral infection disease. Therapy may be the reduction of viral load in a cell, tissue or organism relative to control or prior to administration.

As used in this disclosure, the term "viral infection" is to be understood to mean viruses actively or passively penetrating into, remaining in and subsequently propagating in an organism, such as, for example, a human, an animal or a plant.

As used in this disclosure, the term "viral infectious disease" is to be understood to mean a disease brought about by viruses, illustratively in humans, animals or plants.

As used in this disclosure, the term "disinfection" is to be understood to mean a hygiene measure which serves to bring dead or living material into a state where infection by said material is no longer present. As used in this disclosure, the expression "disinfection" is preferably to be understood to mean a hygiene measure which serves to kill or inactivate pathogens, preferably viruses, or to reduce their number on or in an object or on/in a biological surface.

Therefore, as used in this disclosure, the term "disinfection" can mean in particular an areal disinfection, i.e. a disinfection of areas, optionally surfaces, or a room-air disinfection, i.e. a disinfection of room air. For example, the disinfection can be a disinfection of the room air of an intensive-care unit, an isolation unit, an operating theatre, a laboratory, an airport or an animal husbandry facility.

Provided in this disclosure are composition and processes of using one or more of the composition to treat or prevent infection of a subject by a one or more viruses. A process includes administering to a subject in need of prevention or treatment of viral infection a composition that includes an active ingredient. In some aspects, an active ingredient is or includes a sphingoid compound. Optionally, an active ingredient as provided herein may be used as an active ingredient in a composition alone or with other active or inactive molecules. Optionally, the active ingredient influences, in particular activates or inhibits, the degradation or the generation of a sphingoid base, optionally of sphingosine, in vivo for application or use in the prophylaxis and/or therapy of a viral infection and/or viral infectious disease, in a subject as provided herein or for application or use in disinfection.

In some aspects, an active ingredient is or includes a sphingoid compound. A sphingoid compound is optionally a sphingoid base, or other form of a sphingoid compound suitable for administration to a subject. Optionally, a sphingoid compound is a sphingoid base optionally having the structure of formula I:

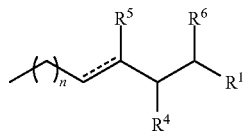

Formula I where $R^1$ means a hydrogen atom, a methyl radical or —$CH_2OR^a$, where $R^a$ is a hydrogen atom, an alkyl radical optionally with a substituent of amine, a quaternary ammonium optionally including 3 hydrogens, or a sugar radical, $R^4$ and $R^5$ independently of one another mean a hydrogen atom, oxygen atom, a hydroxyl group, an amine, or a quaternary ammonium optionally including 3 hydrogens, $R^6$ is an alkyl radical optionally comprising one or more substituents of N, a quaternary ammonium optionally including 3 hydrogens, or

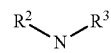

where $R^2$ and $R^3$ independently of one another mean a hydrogen atom or an alkyl radical, n means an integer of from 2 to 50, optionally 5, 6, 7, 8, 9, 10, 11, 12, 13, 14, 15 or 16, and ===== means a double bond or single bond, and/or salts thereof and/or hydrates thereof and/or solvates thereof and/or polymorphs thereof and/or optical isomers, optionally enantiomers and/or diastereomers and/or epimers, thereof and/or mixtures thereof.

In some aspects, a sphingoid compound as provided herein may be or include the following formula I-a

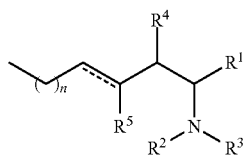

Formula Ia where $R^1$ means a hydrogen atom, a methyl radical or —$CH_2OR^a$, where $R^a$ is a hydrogen atom, an alkyl radical, a quaternary ammonium optionally including 3 hydrogens, or a sugar radical, $R^2$ and $R^3$ independently of one another mean a hydrogen atom or an alkyl radical, $R^4$ and $R^5$ independently of one another mean a hydrogen atom, a hydroxyl group, or a quaternary ammonium optionally including 3 hydrogens, n means an integer of from 2 to 50, optionally 10, 11, 12, 13, 14, 15 or 16, and ╌╌╌╌╌ means a double bond or single bond, and/or salts thereof and/or hydrates thereof and/or solvates thereof and/or polymorphs thereof and/or optical isomers, optionally enantiomers and/or diastereomers and/or epimers, thereof and/or mixtures thereof.

The compound of formula I may be used in the prophylaxis and/or therapy of a viral infection and/or viral infectious disease in a subject as provided herein.

In some aspects, the sphingoid base according to the present disclosure can have or include the following formula I-b:

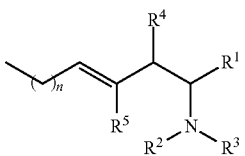

Formula I-b where $R^1$ means a hydrogen atom, a methyl radical or —$CH_2OR^a$, where $R^a$ is a hydrogen atom, an alkyl radical or a sugar radical, or a quaternary ammonium optionally including 3 hydrogens, $R^2$ and $R^3$ independently of one another mean a hydrogen atom or an alkyl radical, $R^4$ and $R^5$ independently of one another mean a hydrogen atom, a hydroxyl group, or a quaternary ammonium optionally including 3 hydrogens, and n means an integer of from 2 to 50, optionally 10, 11, 12, 13, 14, 15 or 16.

Alternatively, the sphingoid base as provided herein can have or include the following formula I-c:

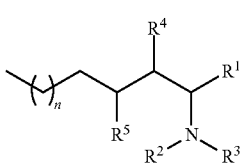

Formula I-c where $R^1$ means a hydrogen atom, a methyl radical or —$CH_2OR^a$, where $R^a$ is a hydrogen atom, an alkyl radical or a sugar radical, $R^2$ and $R^3$ independently of one another mean a hydrogen atom or an alkyl radical, $R^4$ and $R^5$ independently of one another mean a hydrogen atom, oxygen atom, or a hydroxyl group, and n means an integer of from 2 to 50, optionally 10, 11, 12, 13, 14, 15 or 16.

The sphingoid base according to formula I can in principle be a naturally occurring sphingoid base or a non-naturally occurring sphingoid base.

Furthermore, the sphingoid base as provided herein can have chiral centers, optionally chiral carbon atoms, having the absolute configuration R or S or R,S or d,D or l,L or d,l or D,L.

Furthermore, the sphingoid base can be a O-threo isomer, L-threo isomer or an L-erythro isomer of the sphingoid base according to formula I, I-a, I-b, or I-c.

Furthermore, $R^a$ in the formula I can be a linear (i.e. unbranched), or branched alkyl radical, optionally having one to four carbon atoms. As an illustrative non-limiting example, the alkyl radical can be a methyl radical, an ethyl radical, a propyl radical, an isopropyl radical, a butyl radical, a sec-butyl radical or a butyl radical.

In some aspects, $R^a$ in the formula I is a hydrogen atom. In other words, $R^1$ in the formula I, I-a, I-b, or I-c optionally is $CH_2OH$.

The sphingoid base according to formula I can include at least 2 carbon atoms, optionally at least 6 carbon atoms. In some aspects, the sphingoid base can include 18 carbon atoms to 50 carbon atoms. Optionally, the sphingoid base according to formula I, I-a, I-b, or I-c includes 18 carbon atoms.

Alternatively, $R^1$ in the formula I can mean a hydrogen atom (H), a methyl radical ($CH_3$), $CH_2OCH_3$, $CH_2$—O-galactosyl or $CH_2$—O-glucosyl.

As already mentioned, $R^a$ in the formula I can also mean a sugar radical. The sugar radical can, for example, mean a monosaccharide radical, optionally a pentose or hexose radical. Optionally, the sugar radical is present in ring form, optionally as furanose or pyranose.

The sugar radical can, for example, be an arabinose radical, ribose radical, xylose radical, allulose radical, aldotriose radical, fructose radical, galactose radical, glucose radical, gulose radical, inositol radical, mannose radical, or sorbose radical.

Optionally, $R^2$ and $R^3$ in the formula I both mean a hydrogen atom.

Optionally, $R^4$ in the formula I is a hydroxyl group and $R^5$ in the formula I is a hydrogen atom.

In some aspects, the sphingoid base has the following formula II:

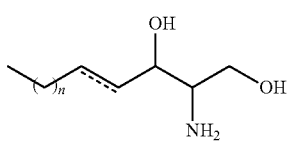

Formula II where
n means an integer of from 2 to 50, optionally 10, 11, 12, 13, 14, 15 or 16, and ╌╌╌╌╌ means a double bond or single bond.

Accordingly, the sphingoid base can have the following formula II-$a_0$:

Formula II-a₀

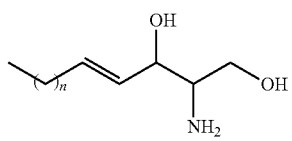

where n means an integer of from 2 to 50, optionally 10, 11, 12, 13, 14, 15 or 16.

Alternatively, the sphingoid base can have the following formula II-a₀*:

Formula II-a₀*

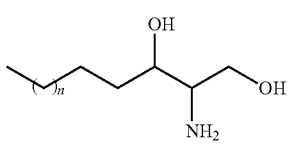

where n means an integer of from 2 to 50, optionally 10, 11, 12, 13, 14, 15 or 16.

In some aspects, the sphingoid base according to formula I is sphingosine, dihydrosphingosine, phytosphingosine, dehydrophytosphingosine, salts thereof, hydrates thereof, solvates thereof, polymorphs thereof, optical isomers, optionally enantiomers and/or diastereomers and/or epimers, thereof, or mixtures of at least two of the aforementioned sphingoid bases.

Optionally, the sphingoid base according to formula I is sphingosine, optionally D-sphingosine, D-erythro-sphingosine or (2S,3R,4E)-2-amino-4-octadecene-1,3-diol, according to the following formula II-a:

Formula II-a

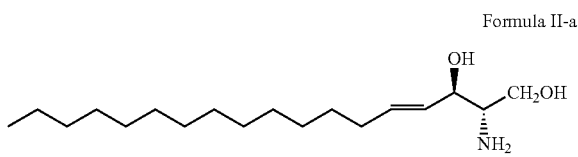 [SMILES: CCCCCCCCCCCCC/C=C/[C@@H](O)[C@@H](N)CO]

Alternatively or in combination, the sphingoid base according to formula I is dihydrosphingosine, optionally D-erythro-dihydrosphingosine or (2S,3R)-2-aminooctadecane-1,3-diol, according to the following formula II-b:

Formula II-b

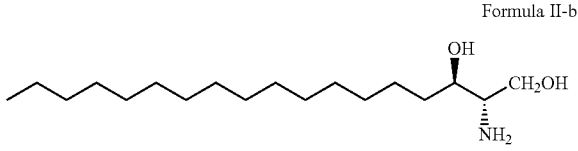 [SMILES: CCCCCCCCCCCCCCC[C@@H](O)[C@@H](N)CO]

Alternatively or in combination, the sphingoid base according to formula I is phytosphingosine, optionally 4D-hydroxysphinganine, (2S,3S,4R)-2-aminooctadecane-1,3,4-triol, according to the following formula II-c:

Formula II-c

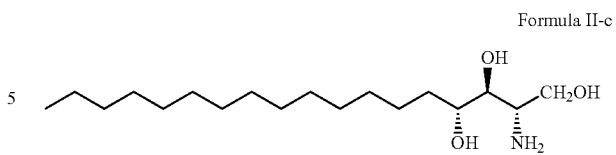

Alternatively or in combination, the sphingoid base according to formula I is dehydrophytosphingosine, optionally D-erythro-dehydrophytosphingosine or (8E)-2-aminooctadec-8-ene-1,3,4-triol or 4R-hydroxysphing-8E-enine, according to the following formula II-d:

Formula II-d

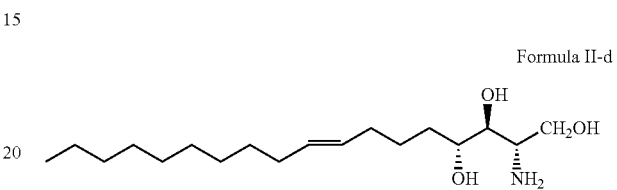

Alternatively or in combination, the sphingoid base according to formula I can be a non-natural isomer of sphingosine, dihydrosphingosine, phytosphingosine or dehydrophytosphingosine.

Optionally, the sphingoid base according to formula I can be D-erythro-C20-sphingosine according to the following formula II-e:

Formula II-e

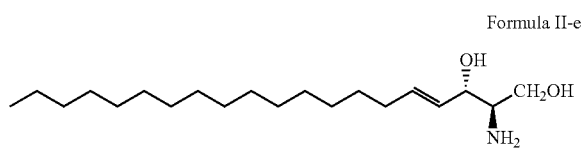 [SMILES: CCCCCCCCCCCCCCC/C=C/[C@H](O)[C@H](N)CO]

Alternatively or in combination, the sphingoid base according to formula I can be D-threo-sphingosine according to the following formula II-f:

Formula II-f

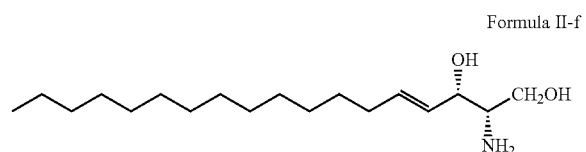

Alternatively or in combination, the sphingoid base according to formula I can be L-threo-dihydrosphingosine according to the following formula II-g:

Formula II-g

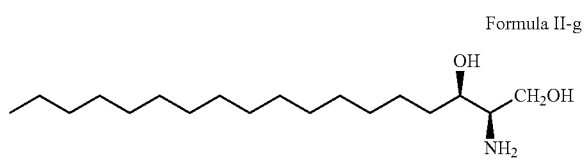 [SMILES: CCCCCCCCCCCCCCC[C@@H](O)[C@H](N)CO]

Alternatively or in combination, the sphingoid base according to formula I can be D-erythro-sphingosine according to the following formula II-h:

Formula II-h

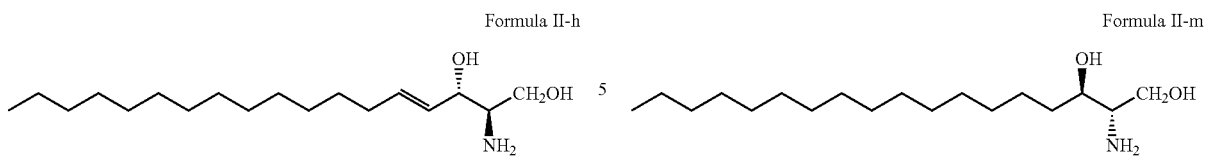

Alternatively or in combination, the sphingoid base according to formula I can be D-threo-dihydrosphingosine according to the following formula II-i:

Formula II-i

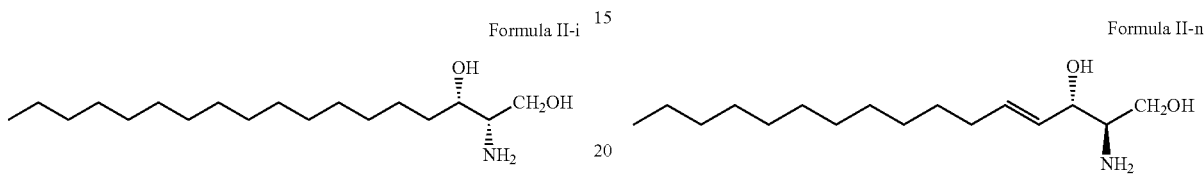

Alternatively or in combination, the sphingoid base according to formula I can be 3-deoxy-D-erythro-sphingosine according to the following formula II-j:

Formula II-j

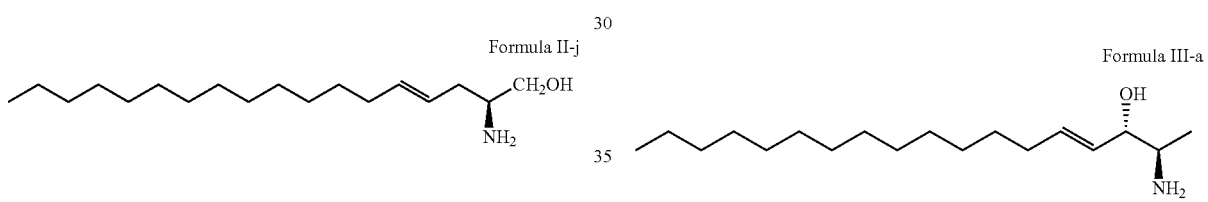

Alternatively or in combination, the sphingoid base according to formula I can be D-erythro-dihydrosphingosine according to the following formula II-k:

Formula II-k

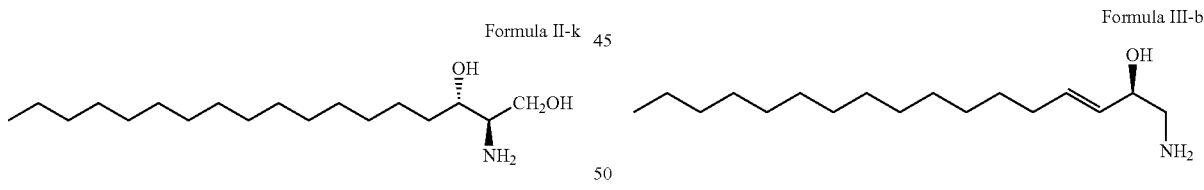

Alternatively or in combination, the sphingoid base according to formula I can be L-threo-sphingosine according to the following formula II-l:

Formula II-l

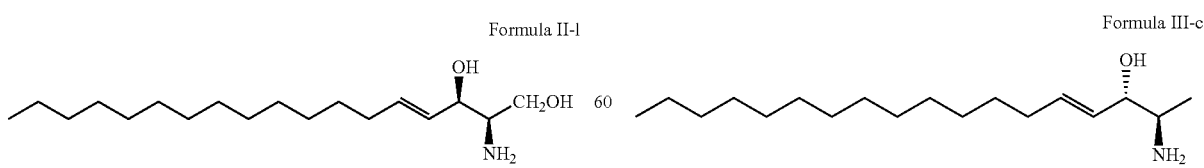

Alternatively or in combination, the sphingoid base according to formula I can be L-erythro-dihydrosphingosine according to the following formula II-m:

Formula II-m

Alternatively or in combination, the sphingoid base according to formula I can be D-erythro-C16-sphingosine according to the following formula II-n:

Formula II-n

Alternatively or in combination, the sphingoid base according to formula I can be 1-deoxy-D-erythro-dihydrosphingosine according to the following formula III-a:

Formula III-a

Alternatively or in combination, the sphingoid base according to formula I can be 1-deoxymethylsphingosine according to the following formula III-b:

Formula III-b

Alternatively or in combination, the sphingoid base according to formula I can be 1-deoxy-D-erythro-sphingosine according to the following formula III-c:

Formula III-c

Alternatively or in combination, the sphingoid base according to formula I can be monomethyl-D-erythro-sphingosine according to the following formula III-d:

Formula III-d

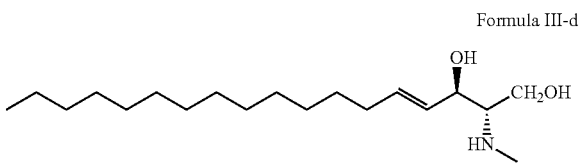 [SMILES: CCCCCCCCCCCCC/C=C/[C@@H](O)[C@H](CO)NC]

Alternatively or in combination, the sphingoid base according to formula I can be galactosylsphingosine according to the following formula III-e:

Formula III-e

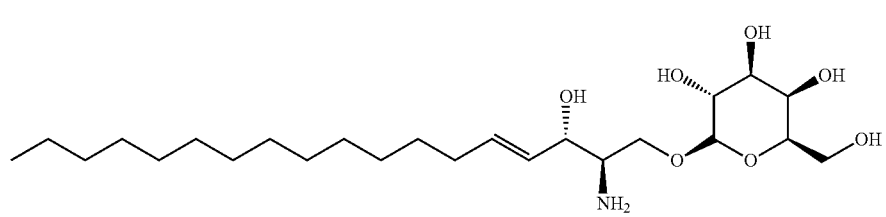

Alternatively or in combination, the sphingoid base according to formula I can be D-erythro-C20-sphingosine, L-erythro-sphingosine, D-threo-dihydrosphingosine (D-threo-sphinganine), L-threo-dihydrosphingosine (L-threo-sphinganine), 1-deoxy-D-erythro-dihydrosphingosine, 1-deoxymethylsphingosine, monomethyl-D-erythro-sphingosine, glucosylsphingosine, D-erythro-dihydrosphingosine (D-erythro-sphinganine), L-erythro-dihydrosphingosine (L-erythro-sphinganine), D-threo-dihydrosphingosine (D-threo-sphinganine), L-threo-dihydrosphingosine (L-threo-sphinganine) or mixtures of at least two of the aforementioned sphingoid bases.

In some aspects, a composition includes a sphingoid compound, but excludes other compounds or compositions that function as an antiviral or otherwise reduce infection or inhibit one or more aspects of the life cycle of a virus, optionally rhinovirus. Optionally, a composition consists of a sphingoid compound, optionally a sphingoid base, optionally sphingosine, and non-functional additives where non-functional means additives that alone do not reduce, treat, or prevent infection by a virus, optionally rhinovirus.

The inventors further discovered on the basis of in vitro experiments that, surprisingly, the addition of an enzyme that catalyzes the generation or production of a sphingoid base, optionally sphingosine, is likewise suitable for treating or preventing a viral infection and is thus suited to preventing a viral infectious disease and/or to treating a viral infection and/or viral infectious disease.

In some aspects of this disclosure, the active ingredient is an enzyme that catalyzes the generation or production of a sphingoid base, optionally of sphingosine. Optionally, the active ingredient is ceramidase, illustratively but not limited to acid, neutral or alkaline ceramidase. Alternatively or in combination, the active ingredient is sphingosine-1-phosphate phosphatase. Furthermore, the active ingredient can be a mixture of at least two of the enzymes mentioned in this paragraph.

In some aspects, the active ingredient is an activator of an enzyme that directly or indirectly catalyzes the generation or production of a sphingoid base, optionally of sphingosine. The expression "activator" is to be understood in this connection in the context of the present disclosure to mean a compound capable of activating or stimulating such an enzyme, optionally the catalytic activity thereof, in some way. In particular, the activator can be a compound that activates or stimulates the expression, optionally the transcription and/or the translation, and/or a post-translational modification, of the enzyme.

Optionally, the activator is a ceramidase activator and/or sphingomyelinase activator and/or a sphingosine-1-phosphate phosphatase activator, or any combination thereof. For example, the activator can be an activator of acid ceramidase, of neutral ceramidase, of alkaline ceramidase, a sphingomyelinase, or of sphingosine-1-phosphate phosphatase.

Furthermore, the activator can be a mixture of at least two of the activators mentioned in this paragraph.

In some aspects of this disclosure, the active ingredient is an inhibitor of an enzyme that directly or indirectly catalyzes the degradation of a sphingoid base, optionally of sphingosine. The expression "inhibitor" is to be understood in this connection in the context of the present disclosure to mean a compound that inhibits or reduces the activity of the enzyme, optionally the catalytic activity thereof, in some way. Optionally, the inhibitor can be a compound that inhibits or reduces the expression, optionally the transcription and/or the translation and/or a post-translational modification, of the enzyme.

Optionally, the inhibitor is a sphingosine kinase inhibitor or a ceramide synthase (CerS) inhibitor. For example, the inhibitor can be an inhibitor of sphingosine kinase 1, of sphingosine kinase 2, of ceramide synthase 1, of ceramide synthase 2, of ceramide synthase 3, of ceramide synthase 4, or ceramide synthase 5, of ceramide synthase 6, or any combination thereof. Furthermore, the inhibitor can be a mixture of at least two of the inhibitors mentioned in this paragraph.

The inhibitor, optionally ceramide synthase inhibitor, can be Fingolimod or a derivative thereof, optionally as disclosed in Schiffmann, et al., *Biochimie,* 2012; 94(2):558-65, P053 as found in Turner, et al., *Nature Communication,* 2018; Article number: 3165.

Optionally, the inhibitor is an inhibitor of sphingosine kinase 1 and/or an inhibitor of sphingosine kinase 2.

In some aspects, the inhibitor is a sphingosine kinase 1 inhibitor, optionally selected from the group consisting of (2R,3S,4E)-N-methyl-5-(4-pentylphenyl)-2-aminopent-4-ene-1,3-diol, (R)-(1-(4-((3-methyl-5-(phenylsulfonylmethyl)phenoxy)methyl)benzyl)pyrrolidin-2-yl)methanol, (2,2-dimethyl-4S-(1-oxo-2-hexadecyn-1-yl)-1,1-dimethylethyl ester-3-oxazolidinecarboxylic acid, (N'-[1-(3,4-dimethoxyphenyl)ethylidene]-3-(4-methoxyphenyl)-1H-pyrazole-5-carbohydrazide), Compound 82 (Amgen), amidine-based inhibitors such as VPC94075 and CB5468139, and mixtures of at least two of the aforementioned inhibitors.

Optionally, the inhibitor is a sphingosine kinase 2 inhibitor optionally selected from the group consisting of ABC294640, [3-(2-aminoethyl)-5-[3-(4-butoxylphenyl)propylidene]thiazolidine-2,4-dione], synthetic sphingosine analogues SG12 and SG14, (R)-FTY720-OMe, (S)-2-(3-(4-octylphenyl)-1,2,4-oxadiazol-5-yl)pyrrolidine-1-carboximidamide, (S)-2-(3-(4-octylphenyl)-1,2,4-oxadiazol-5-yl)azetidine-1-carboximidamide hydrochloride, and mixtures of at least two of the aforementioned inhibitors.

In some aspects, the inhibitor is a sphingosine kinase 1 inhibitor and/or sphingosine kinase 2 inhibitor, optionally selected from the group consisting of SKI-II ([2-(p-hydroxyanilino)-4-(p-chlorophenyl)thiazole]), SK1-I ((2R,3S,4E)-N-methyl-5-(4-pentylphenyl)-2-aminopent-4-ene-1,3-diol), MP-A08 and mixtures of at least two of the aforementioned inhibitors.

In principle, the sphingoid base and/or the active ingredient can be prepared for a local or systemic administration.

Optionally, the sphingoid base and/or the active ingredient is prepared for an intravenous, intra-arterial, cutaneous, subcutaneous, percutaneous, intramuscular, inhalational, intravaginal, oral, nasal or conjunctival administration. In other words, the sphingoid base and/or the active ingredient may be used for an intravenous, intra-arterial, cutaneous, subcutaneous, percutaneous, intramuscular, inhalational, intravaginal, oral, nasal or conjunctival administration.

Optionally, administration is an intravenous or nasal administration. An intravenous administration may result in a systemic and thus extensive prophylactic and/or therapeutic action. A nasal administration may result in a rapid onset of action and may directly target the site of infection of some viruses, illustratively rhinoviruses. Moreover, with both forms of administration, a further advantage is that just a low dose may be sufficient to achieve a desired action.

Optionally, the prophylaxis is, in the context of the present disclosure, a vaccination and/or an improvement in success of vaccination against a viral infection and/or viral infectious disease.

The sphingoid base and/or the active ingredient can be prepared for an administration in a dose of from 0.001 mg/kg body weight to 10 mg/kg body weight, optionally 0.01 mg/kg body weight to 1 mg/kg body weight, optionally 0.1 mg/kg body weight, or be used for such an administration at such dose.

Optionally, the viral infection and/or viral infectious disease is a viral infection and/or viral infectious disease in a human, i.e. a human viral infection and/or human viral infectious disease.

Optionally, the viral infection and/or viral infectious disease is haemorrhagic fever, haemorrhagic fever with renal syndrome (HFRS), encephalitis, meningoencephalitis, tick-borne encephalitis (TBE), lymphocytic choriomeningitis, Lassa fever, herpes simplex type 1, herpes simplex type 2, hepatitis B, herpes zoster, glandular fever, cytomegaly, acquired immunodeficiency syndrome (AIDS), severe acute respiratory syndrome, smallpox, rubella, hepatitis C, Zika fever, West Nile fever, dengue fever, yellow fever, Rift Valley fever, sandfly fever, Marburg fever, Ebola, influenza, brain inflammation, measles, mumps, respiratory virus disease, BK nephropathy, hepatitis C, poliomyelitis, viral meningitis, or myocarditis.

Optionally, the viral infection and/or viral infectious disease can be a viral infection and/or viral infectious disease which is/are brought about or caused by enveloped viruses, selected in particular from the group consisting of Arenaviridae, Herpesviridae, Retroviridae, Coronaviridae, Poxviridae, Togaviridae, Flaviviridae, Bunyaviridae, Filoviridae, Orthomyxoviridae, Paramyxoviridae and Rhabdoviridae.

The Arenaviridae can be selected from the group consisting of Lassa virus, Junin virus and lymphocytic choriomeningitis virus (LCMV).

The Herpesviridae can be selected from the group consisting of herpes simplex virus, hepatitis B virus, varicella-zoster virus, cytomegalovirus and Epstein-Barr virus.

The Retroviridae can, for example, be the human immunodeficiency virus or the human T-lymphotropic virus.

The Poxviridae can, for example, be the smallpox virus.

The Togaviridae can, for example, be the rubella virus or the Semliki Forest virus.

The Flaviviridae can be selected from the group consisting of hepatitis C virus, Zika virus, West Nile virus, dengue virus, yellow fever virus and TBE virus.

The Bunyaviridae can be selected from the group consisting of Rift Valley fever virus, sandfly fever virus and Hantaan virus.

The Filoviridae can, for example, be the Marburg virus or Ebola virus.

The Orthomyxoviridae can, for example, be selected from the group consisting of influenza virus A, influenza virus B and influenza virus C.

The Paramyxoviridae can be selected from the group consisting of Nipah virus, human parainfluenza virus, measles virus and mumps virus.

The Rhabdoviridae can, for example, be the vesicular stomatitis virus or rabies virus.

In particular, the viral infection and/or viral infectious disease can be a viral infection and/or viral infectious disease in a human, i.e. a human viral infection and/or human viral infectious disease, which is/are brought about or caused by non-enveloped viruses, optionally Adenoviridae, Polyomaviridae, Papillomaviridae, Hepeviridae, or rhinovirus.

The Adenoviridae can, for example, be the human adenovirus.

The Polyomaviridae can, for example, be the BK virus.

The Papillomaviridae can, for example, be the human papillomavirus.

The Hepeviridae can, for example, be the hepatitis E virus.

The Picornaviridae can, for example, be the poliovirus, coxsackievirus or the enterovirus.

The virus can, for example, be human rhinovirus.

In some aspects, the viral infection and/or viral infectious disease is a viral infection and/or viral infectious disease in a non-human animal, such as, for example, a dog, a cat, a horse, a cow, a pig, a bird, a fish, a reptile, an amphibian, a mollusc, an insect or a spider.

The viral infection and/or viral infectious disease is/are optionally monkeypox, African horse sickness, African swine fever, equine infectious anaemia (swamp fever), infectious salmon anaemia, Aujeszky's disease in domestic cattle and/or domestic pigs, bluetongue disease, bovine herpesvirus type 1 infections, bovine viral diarrhoea, common cold, Ebola virus infection, epizootic haemorrhage in deer, epizootic haematopoietic necrosis, enzootic leukosis in cattle, avian influenza (bird flu), West Nile virus infection in birds and/or horses, koi herpesvirus infection in carp, foot-and-mouth disease, Newcastle disease, peste des petits ruminants (ovine rinderpest), equine encephalomyelitis, sheep and goat pox, Rift Valley fever, rinderpest, swine fever (European swine fever), vesicular stomatitis, Taura syndrome, rabies, swine vesicular disease, viral haemorrhagic septicaemia in Salmonidae, white spot disease in crustaceans, or yellowhead disease, optionally in shrimp and prawns.

Optionally, the viral infection and/or viral infectious disease can be a viral infection and/or viral infectious disease that is/are brought about or caused by the monkeypox virus, African horse sickness virus (AHS), African swine fever virus, equine infectious anaemia virus, infectious salmon anaemia virus, Aujeszky's disease virus, bluetongue virus, bovine herpesvirus type 1, bovine viral diarrhoea virus, Ebola virus, epizootic haemorrhagic disease virus (EHDV), rhabdovirus, bovine leukaemia virus, influenza virus, West Nile virus, koi herpesvirus, foot-and-mouth disease virus, Newcastle disease virus, *Capripoxvirus ovis*, *Capripoxvirus caprae*, phleboviruses, rinderpest virus, vesicular stomatitis virus, Taura syndrome virus, rabies virus, swine vesicular disease virus, white spot disease virus or yellowhead virus.

In some aspects, the viral infection and/or viral infectious disease is a viral infection and/or viral infectious disease of a plant, i.e. a plant viral infection and/or plant viral infectious disease, selected in particular from the group consisting of tomato spotted wilt disease, impatiens necrotic spot disease, pepino mosaic disease, zucchini yellow mosaic disease, papaya ringspot disease, watermelon mosaic disease, Moroccan watermelon mosaic disease, potato virus A disease, tobacco rattle disease, potato virus Y disease, squash mosaic disease, cucumber green mottle mosaic disease, tobacco ringspot disease, tomato ringspot disease, tobacco mosaic disease and tobacco necrosis.

Optionally, the viral infection and/or viral infectious disease can be a viral infection and/or viral infectious disease in a plant that is/are brought about or caused by the tomato spotted wilt virus, *impatiens* necrotic spot virus, pepino mosaic virus, zucchini yellow mosaic virus, *papaya* ringspot virus, watermelon mosaic virus, Moroccan watermelon mosaic virus, potato virus Y, potato virus A, tobacco rattle virus, squash mosaic virus, cucumber green mottle mosaic virus, tobacco ringspot virus, tomato ringspot virus, tobacco mosaic virus or tobacco necrosis virus.

In some aspects, provided is a medicament (drug) or a pharmaceutical composition for application or use in the prophylaxis and/or therapy of a viral infection and/or viral infectious disease or for application or use in disinfection.

The medicament or the pharmaceutical composition comprises a sphingoid compound and/or an active ingredient that influences, in particular activates or inhibits, the degradation or the generation of a sphingoid base, optionally of sphingosine, in vivo.

Optionally, the medicament or the pharmaceutical composition further comprises pharmaceutically acceptable carriers for the sphingoid compound and/or the active ingredient. The carrier can, for example, be selected from the group consisting of water, acetone, ethanol, ethylene glycol, propylene glycol, butane-1,3-diol, isopropyl myristate, isopropyl palmitate, liposomes, mineral oil and mixtures of at least two of the carriers mentioned.

Furthermore, the medicament or the pharmaceutical composition can further include a surface-active substance, such as, for example, n-octyl-β-D-glucopyranoside (OGP).

In principle, the medicament or the pharmaceutical composition can be formulated for a local or systemic administration or be present in a local or systemic form of administration.

In some aspects, the medicament or the pharmaceutical composition is formulated as a solution, a colloidal dispersion, an emulsion (oil-in-water emulsion or water-in-oil emulsion), a suspension, a cream, a lotion, a gel, a foam, a spray, an aerosol, an ointment, tablets, drops or a suppository. In other words, the medicament or the pharmaceutical composition is optionally present in the form of a solution, a colloidal dispersion, an emulsion (oil-in-water emulsion or water-in-oil emulsion), a suspension, a cream such as skin cream, a lotion, a gel, a foam, a spray such as nasal spray, an aerosol, an ointment, tablets, drops or a suppository.

Optionally, the medicament or the pharmaceutical composition is a skin cream, i.e. a cream for application to the skin or mucosa, or a medicament/pharmaceutical composition prepared for a nasal administration, or a medicament/pharmaceutical composition prepared for ocular administration. Optionally, the medicament or the pharmaceutical composition can be a nasal spray, a nasal ointment or nasal drops. Optionally, the medicament or pharmaceutical composition can be an eye drop or other known method.

In some aspects, the medicament or the pharmaceutical composition can include a proportion of the sphingoid base and/or the active ingredient of from 0.01% by weight to 100% by weight, optionally 0.1% by weight to 30% by weight, and optionally 1% by weight to 10% by weight, based on the total weight of the medicament or the pharmaceutical composition.

With regard to further features and advantages of the sphingoid base and/or the active ingredient, full reference is made to the remarks made in the context of the disclosure above in order to avoid repetition. The features and advantages described there with regard to the sphingoid base and/or the active ingredient also apply mutatis mutandis to a medicament or drug or a pharmaceutical composition.

Also provided are the use of a sphingoid base as a food or food supplement.

The food or food supplement includes a sphingoid base and/or an active ingredient.

In the context of the present disclosure, the term "food" is to be understood to mean a food which serves for the nutrition of a human or non-human animal.

In the context of the present disclosure, the expression "food supplement" is to be understood to mean a product for the supplemental nutrition of a human and/or for the increased or improved supply of nutrients or active ingredients to human metabolism.

With regard to further features and advantages of the sphingoid base and/or the active ingredient, full reference is made to the remarks made in the context of the disclosure above in order to avoid repetition. The features and advantages described elsewhere herein with regard to the sphingoid base and/or the active ingredient also apply mutatis mutandis to a food or food supplement as also provided herein.

Also provided herein is a feed or feed supplement. The feed or feed supplement includes a sphingoid base and/or an active ingredient as provided herein. In the context of this disclosure, the term "feed" is to be understood to mean a product for the nutrition of non-human animals, optionally non-human mammals, birds or fishes, i.e. a so-called animal food. For example, the feed can be a feed for fishes, optionally aquarium fishes. Alternatively, the feed can be a feed for dogs, cats, horses, cows, pigs, or other non-human animal.

As used herein, the term "feed supplement" is to be understood to mean a product for the supplemental nutrition of non-human animals, optionally non-human mammals, birds or fishes, and/or for the increased or improved supply of nutrients or active ingredients to the metabolism of non-human animals, optionally non-human mammals, birds or fishes. For example, the feed supplement can be a feed supplement for fishes, optionally aquarium fishes, or other non-human animals.

Also provided herein is a plant protection agent. The plant protection agent includes a sphingoid base and/or an active ingredient as otherwise described herein. For example, the plant protection agent can be a plant protection agent for cultivated plants, illustratively wheat, rapeseed, tomatoes, or the like. With regard to further features and advantages of the sphingoid base and/or the active ingredient, full reference is made to the remarks made in the context of the disclosure above in order to avoid repetition. The features and advantages described there with regard to the sphingoid base and/or the active ingredient also apply mutatis mutandis to a plant protection agent as provided herein.

Optionally, as provided herein a sphingoid base of formula I is used for application or use in the inhibition or hindering of bacteriophages or for application or use in the stabilization and/or spreading of a bacterial flora, optionally healthy bacterial flora, or for application or use in the avoidance of the formation of resistant bacterial strains.

Optionally, medicament or the pharmaceutical composition is an active ingredient that influences, optionally activates or inhibits, the degradation or the generation of a sphingoid base, optionally of sphingosine, in vivo for application or use in the inhibition or hindering of bacteriophages or for application or use in the stabilization and/or spreading of a bacterial flora, optionally healthy bacterial flora, or for application or use in the avoidance of the formation of resistant bacterial strains.

The above-mentioned bacterial flora can, for example, be a skin or mucosa, optionally intestinal mucosa. Furthermore, the skin can be a human skin or a skin of a non-human animal, optionally a non-human mammal or a bird.

With regard to further features and advantages of the sphingoid base and/or the active ingredient, full reference is made to the remarks made in the context of the disclosure above in order to avoid repetition. The features and advantages described there with regard to the sphingoid base and/or the active ingredient also apply mutatis mutandis to the application or use of the sphingoid base and/or the active ingredient for application or use in the inhibition or hindering of bacteriophages or for application or use in the stabilization and/or spreading of a bacterial flora, optionally healthy bacterial flora, or for application or use in the avoidance of the formation of resistant bacterial strains.

According to some aspects provided optionally for in vitro use is a sphingoid base of the following formula I for the inhibition or hindering of bacteriophages or for the stabilization and/or spreading of a bacterial flora, optionally healthy bacterial flora, or for the avoidance of the formation of resistant bacterial strains.

The above-mentioned bacterial flora can, for example, be a skin or mucosa, optionally intestinal mucosa. Furthermore, the skin can be a human skin or a skin of a non-human animal, optionally a non-human mammal or a bird.

With regard to further features and advantages of the sphingoid base and/or the active ingredient, full reference is made to the remarks made in the context of the disclosure above in order to avoid repetition. The features and advantages described herein with regard to the sphingoid base and/or the active ingredient also apply mutatis mutandis to the use of a sphingoid base and/or an active ingredient for in vitro use.

Further features and advantages of the disclosure are revealed by the following description of preferred embodiments in the form of exemplary embodiments, the associated figures and the claims. The embodiments described below merely serve for further elucidation and for better understanding of the disclosure and are in no way to be understood as limiting.

EXPERIMENTAL SECTION

1. Methods and Materials
1.1 Mice and Tamoxifen Treatment

For in vivo analyses, Asah1$^{-/-}$ mice, from which acid ceramidase was genetically removed, were used. Asah1$^{-/-}$ mice were on a C57BL/6J background. As control animals, sibling animals with the genotype Asah1$^{+/+}$ were used. Inducible ceramidase-deficient animals were used (Cre$^+$ Asah1$^{fl/fl}$). Inducible ceramidase-deficient animals expressed a Cre recombinase under the tamoxifen promoter and the gene Asah1 between two LoxP sites. Administration of tamoxifen thus led to the expression of the recombinase, which then removed the Asah1 gene. Tamoxifen was dissolved in corn oil. Eight, six and four days before an experiment, Cre$^-$×Asah1$^{fl/fl}$ control animals and Cre$^+$ Asah1$^{fl/fl}$ animals were treated intraperitoneally with, in each case, 4 mg of tamoxifen (in 100 µl).

1.2 Cell Lines, Bone Marrow Macrophages and Human T Cells

Raw264.7 and Hela cells were purchased from ATCC. Vero cells and MC57 cells came from the Ontario Cancer Institute. Macrophages were generated by isolating bone marrow from mice and culturing said bone marrow with M-CSF for 9 days. Cells were then plated out onto a new cell culture plate and the experiment was started on the next day. Human T cells were generated by using EDTA-blood samples from healthy donors. CD8 T cells were eliminated, and the remaining CD4 T cells were activated and were cultured until the start of the experiment.

1.3 Viruses

The LCMV strain WE and the VSV strain Indiana were obtained from the laboratory of Prof. Zinkernagel (Institute of Experimental Immunology, Zurich, Switzerland). HSV-1 came from Prof. Beate Sodeik (Institute of Virology, Hanover, Germany). Influenza A came from Prof. Matthias Tenbusch (Institute of Virology, Erlangen, Germany). The Friend retrovirus came from Prof. Ulf Dittmer (Institute of Virology, Essen, Germany). The HIV came from Prof. Hendrik Streeck (Institute for HIV Research). Rhinovirus was from ATCC.

1.4 Reagents

D-erythro-Sphingosine (C18) from Avanti Polar Lipids (860490-25 mg) was used as a sphingoid base. Ceramidase (E 9030-100MUN) and sphingomyelinase (58633-25UN) were purchased from Sigma. Sphingosine kinase inhibitors, MP A08 (CAS #219832-49-2; cat. No. 5803) and SKIT (CAS #: 312636-16-1; cat. No. 2097), came from Tocris.

1.5 Infection of Cells and Animals

For in vitro infection, the virus was added to the cell cultures. After incubation for one hour, the supernatant was washed away and fresh medium was added. The supernatant was removed at different times after infection. For in vitro infections with HSV-1, cell cultures were pre-treated on ice at 4° C. for 20 minutes, and virus was added under these conditions and incubated for one hour. The supernatant was removed, new medium was added, and the cell cultures were stored at 37° C. until analysis. This approach is known as synchronized infection. For an intravenous infection, the virus was injected in 100 µl into the tail vein. For an intranasal infection, the virus was pipetted, in 10 µl each, into each nares of the nose.

1.6 Determination of Virus Propagation by Means of Immunofluorescence

To be able to detect viruses in cells and organs, immunofluorescence was used. For in vitro experiments, cells were seeded into 24-well plates containing coverslips. After 24 hours, the cells were appropriately infected and were fixed after incubation and labelled with antibodies. Organs from infected animals were flash-frozen. 8 μm thick sections were accommodated on a slide. The sections were fixed and viruses were then visualized by means of virus-specific antibodies. The following primary antibodies were used: anti-LCMV-NP antibody (clone VL4); anti-HSV-1-capsid (SY4563, anti-capsid). Alternatively, virus directly labelled with a dye (e.g. CFSE) was used.

1.7 Determination of VSV Virus Propagation

To measure the influence of sphingosine on the propagation of the vesicular stomatitis virus (VSV), Vero cells were seeded in a 24-well plate. Once the cells had grown to confluence, ceramidase or sphingomyelinase was added. Thereafter, the cell lawn was infected with the vesicular stomatitis virus (VSV) (100 PFU/well). After one hour, methylcellulose was added so that virus was able to spread only by cell-cell interaction. The result of this was that only cells in immediate proximity were infected and thus an initial infection was visible via holes in the cell lawn (=plaques). After 24 hours, the number of plaques was ascertained.

1.8 Determination of LCMV in Organs and Cell Supernatant by Means of Plaque Assay To determine virus amount, cell culture supernatant or homogenized organ lysate was titrated in a 24-well plate and soluble MC57 cells (150 000 cells/well) were then added. After 4 hours, MC57 cells were able to adhere, and methylcellulose was added. After a further 48 hours, the cell lawn was analyzed for LCMV plaques using an anti-LCMV-NP antibody (clone VL4). The plaques were counted and thus the number of infectious particles per ml in the supernatant or lysate was determined.

1.9 Determination of IAV in Lungs

To determine the virus amount of the influenza A virus (IAV) from homogenized organ lysate, MDCK2 cells were seeded in a 24-well plate. On the next day, when the cells had grown to confluence, the organ lysates were diluted and added. After two hours, methylcellulose was added so that virus was able to spread only by cell-cell interaction. The result of this was that only cells in immediate proximity were infected and thus an initial infection was visible via holes in the cell lawn (=plaques). After 24 hours, the number of plaques was ascertained and thus the number of infectious particles per ml in the lysate was determined.

1.10 Determination of Friend Virus-Infected Cells

For the analysis of the Friend virus-infected cells, spleens and blood were analyzed. The spleens were mechanically crushed and the cells of the spleens were isolated after filtration. Cells and blood were stained with anti-B220 (label for B cells) and anti-Terr119 (label for erythroid progenitor cells) and subsequently fixed with 2% formalin and then lysed with saponin. Infected cells were ascertained by the expression of wasabi.

1.11 Survival Experiments

To analyze the effect of sphingosine on the course of infection, survival experiments were carried out. To this end, animals were infected with a dose sublethal for WT animals. Animals were checked daily and were killed at relevant termination criteria and counted as dead. The termination criteria were: body weight, general health, spontaneous behavior and clinical findings.

1.12 P24 ELISA and HIV Infection

PBMCs (peripheral blood mononuclear cells) were purified from EDTA-blood samples from healthy donors (Streeck et al., 2007). CD8 T cells were eliminated using CD8 MicroBeads (Miltenyi Biotec) and the remaining cells were activated using 1 μg/ml phytohaemagglutinin (PHA). Activated cells were transferred into a 96-well plate and treated with the substances to be tested. Thereafter, the cells were infected with 63 ng/ml HIV-1 JR-CSF virus for one hour. Using the HIV-1 Gag p24 Quantikine ELISA Kit (R&D Systems), the infection rate was measured on days 4 and 7 after infection. For the evaluation, the NanoQuant Infinite M200 (Tecan) was used.

1.13 Production of Sphingosine-Containing Liposomes

A thin film of poly(vinyl alcohol) PVA was applied to glass iBidi plates. The fat mix was distributed on the plates and the liposomes were incubated at 60° C. for one hour. The fat concentration in the liposomes was as follows:

| | |
|---|---|
| Control liposomes | Ch:PC:Sm (33:33:33 molar) + 0.05 mol % BODIPY_PC |
| Ceramide liposomes | Ch:PC:Sm:Cer (33:33:24:10 mol/%) + 0.05 mol % BODIPY_PC |
| Sphingosine liposomes 1 | Ch:PC:Sm:Sph (33:33:24:10 mol/%) + 0.05 mol % BODIPY_PC |
| Sphingosine liposomes 2 | Ch:PC:Sm:Sph (33:33:14:20 mol/%) + 0.05 mol % BODIPY_PC |

1.14 Statistical Analysis

The means were compared using an unpaired two-tailed Student's t-test. The data were presented as mean±SEM. The statistical significance level was defined at $p<0.05$. Significant differences were marked in the graph with "*".

2. Investigations

2.1

FIG. 1 is a schematic depiction of the natural metabolism of sphingomyelin. Sphingomyelin (SM) is converted into ceramide (CER) by sphingomyelinase (SMase). Ceramide is converted into sphingosine (SPH) by ceramidase (CERase). Sphingosine is phosphorylated by sphingosine kinase (SPH kinase) to form sphingosine-1-phosphate (SPH-1-P). Also illustrated are exemplary enzymes that can alter the concentration of sphingosine as a result of activation or inhibition where sphingomyelinase is denoted (SMase), ceramidase is denoted (CERase), and sphingosine kinase is denoted (SPH-kinase).

2.2

Figure 2:
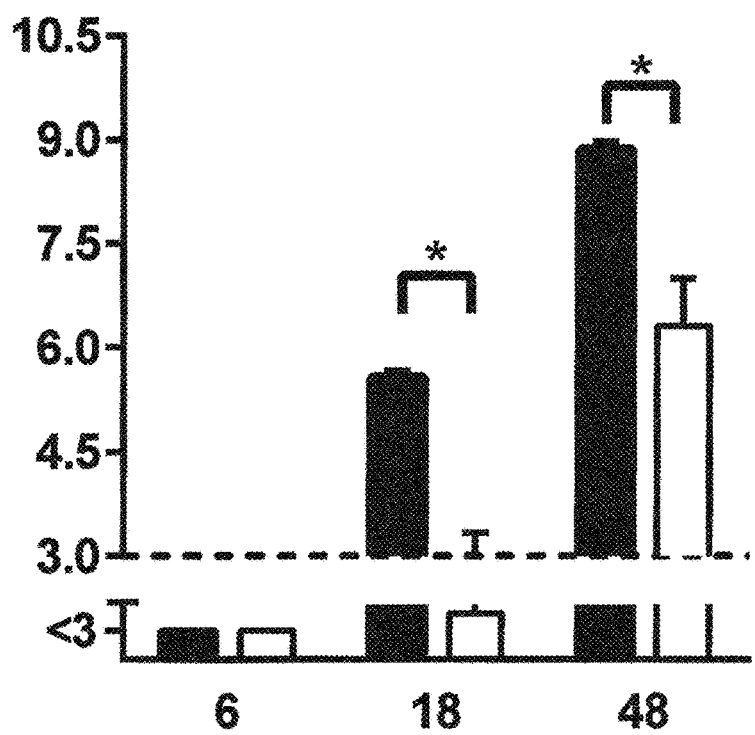
FIG. 2 illustrates the amount of lymphocytic choriomeningitis virus (LCMV) particles in the supernatant of Raw264.7 cells were treated with 250 µM D-erythro-sphingosine for 10 minutes and then infected with the LCMV where the Y-axis: Infectious LCMV particles in the supernatant (PFU/ml, logarithmic scale), the X-axis: is time points of the measurements (in hours after infection); Black bars are control; White bars are sphingosine-treated illustrating that treatment with sphingosine reduced propagation of LCMV.

Raw264.7 cells were treated with 250 μM D-erythro-sphingosine for 10 minutes and then infected with the lymphocytic choriomeningitis virus (LCMV) (MOI: 0.01). After incubation for one hour, the medium was changed and virus production was measured by means of plaque assay after 6, 18 and 48 hours. In this case, it was possible to demonstrate that sphingosine inhibits the propagation of LCMV. The results obtained are depicted graphically in FIG. 2. Shown is the mean±SEM, n=3, *$p<0.05$ student's T test.

2.3

Figure 3:
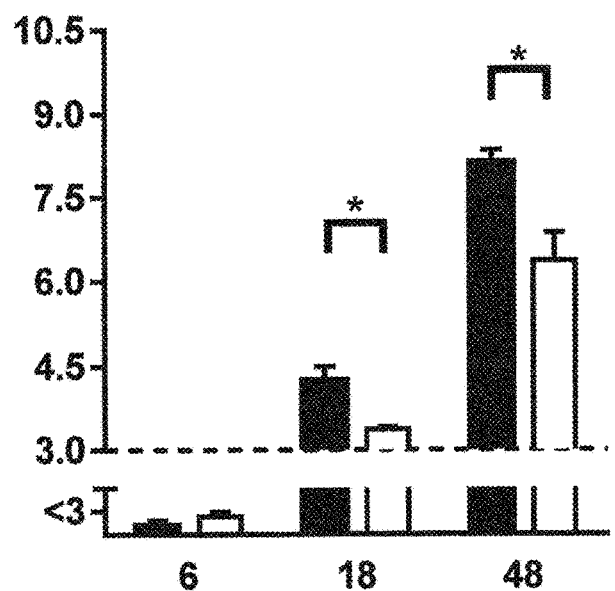
FIG. 3 illustrates the amount of LCMV particles in the supernatant of Raw264.7 cells were treated with ceramidase (250 mUnits/ml) for 10 minutes and then infected with the LCMV (MOI: 0.01) where the Y-axis: Infectious LCMV particles in the supernatant (PFU/ml, logarithmic scale), the X-axis: is time points of the measurements (in hours after infection); Black bars are control; White bars are ceramidase-treated illustrating that treatment with ceramidase reduced propagation of LCMV.

Raw264.7 cells were treated with ceramidase (250 mUnits/ml) for 10 minutes and then infected with the lymphocytic choriomeningitis virus (LCMV) (MOI: 0.01). After incubation for one hour, the medium was changed and virus production was measured by means of plaque assay after 6, 18 and 48 hours. In this case, it was possible to demonstrate that ceramidase inhibits the propagation of LCMV. The results obtained are depicted graphically in FIG. 3. Shown is the mean±SEM, n=5, *$p<0.05$ student's T test.

2.4

Figure 4:
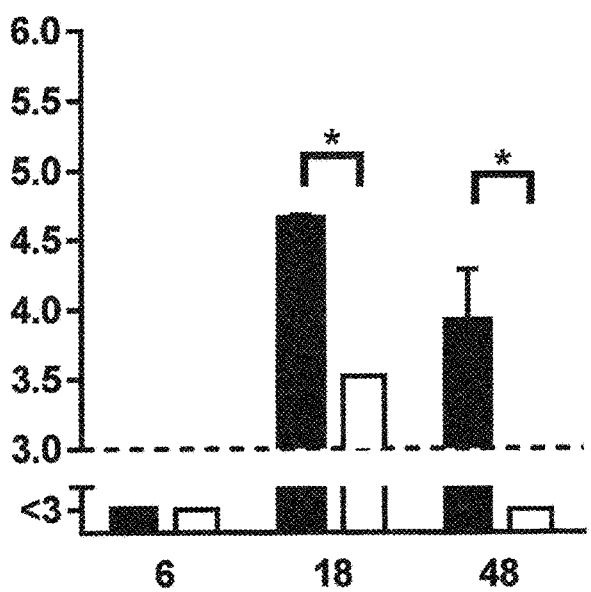
FIG. 4 illustrates the amount of LCMV particles in the supernatant of Raw264.7 cells were treated with sphingomyelinase (6.5 U/ml) for 10 minutes and then infected with the LCMV (MOI: 0.01) where the Y-axis: Infectious LCMV particles in the supernatant (PFU/ml, logarithmic scale), the X-axis: is time points of the measurements (in hours after infection); Black bars are control; White bars are ceramidase-treated illustrating that treatment with ceramidase reduced propagation of LCMV.

Raw264.7 cells were treated with sphingomyelinase (6.5 U/ml) for 10 minutes and then infected with the lymphocytic choriomeningitis virus (LCMV) (MOI 0.01). After incubation for one hour, the medium was changed and virus production was measured by means of plaque assay after 6, 18 and 24 hours. In this case, it was possible to demonstrate that sphingomyelinase inhibits the propagation of LCMV. The results obtained are depicted graphically in FIG. 4. Shown is the mean±SEM, n=3, *p<0.05 student's T test.

2.5

Figure 5:
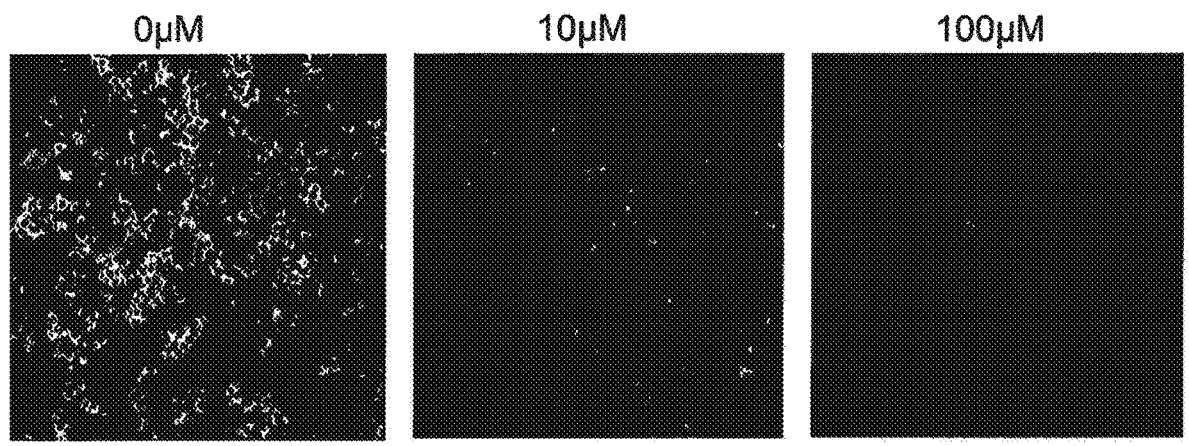
FIG. 5 illustrates Hela cells treated with 10 micromolar (µM) and 100 µM sphingosine kinase inhibitor SKII and infected with the LCMV illustrating that inhibition of sphingosine kinase inhibits spreading of the virus.

Hela cells were treated with the sphingosine kinase inhibitor SKII (10 μM and 100 μM) for 10 minutes. Cells were infected with the lymphocytic choriomeningitis virus (LCMV) (MOI 1). After 24 hours, virus-infected cells were measured by means of immunofluorescence. In this case, it was possible to demonstrate that sphingosine kinase inhibition inhibits the spreading of the virus. The results obtained are depicted as immunofluorescence images in FIG. 5 where white are the LCMV-infected cells in cultures without sphingosine kinase inhibitor (0 μM), with 10 μM sphingosine kinase inhibitor and with 100 μM sphingosine kinase inhibitor (n=5).

2.6

Figure 6:
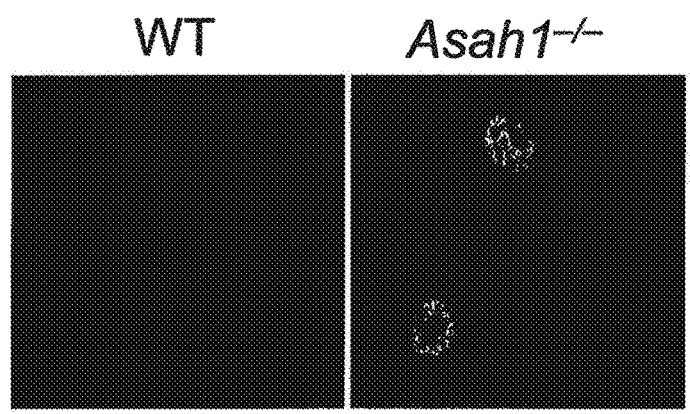
FIG. 6 illustrates macrophages from wild-type (WT) mice and ceramidase-deficient mice (Asah1$^{-/-}$) and then infected with herpes simplex virus (HSV-1) (MOI 5) illustrating that ceramidase deficiency promotes the spreading of the virus.

Macrophages were obtained from the bone marrow of WT mice and ceramidase-deficient mice (Asah1$^{-/-}$) and then infected with herpes simplex virus (HSV-1) (MOI 5). After 4 hours, the propagation of the virus was measured by means of immunofluorescence. In this case, it was possible to demonstrate that ceramidase deficiency promotes the spreading of the virus. The results obtained are depicted as immunofluorescence images in FIG. 6. Shown in white are HSV-1 in nuclei of infected wild-type (WT) cells and ceramidase-deficient (Asah1$^{-/-}$) cells (n=4).

2.7

Figure 7:
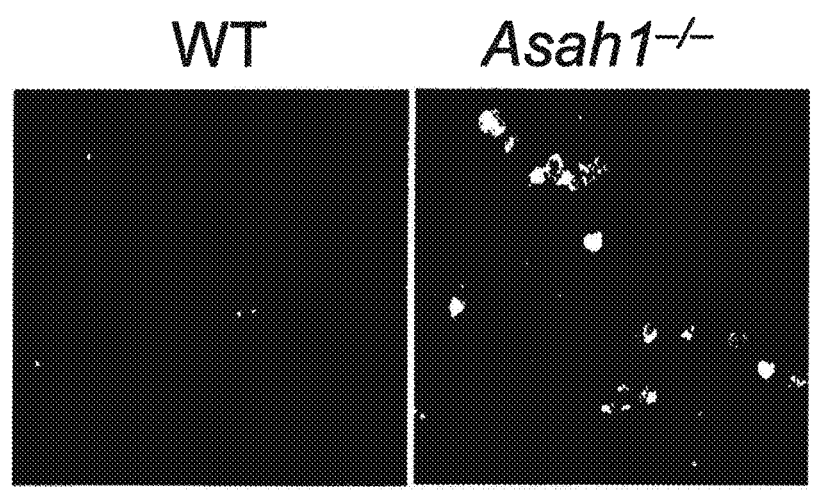
FIG. 7 illustrates propagation of herpes simplex virus (HSV-1) in WT mice and ceramidase-deficient mice (Asah1$^{-/-}$) demonstrating that ceramidase deficiency promotes the spreading of the virus in the liver of HSV-1 infected animals.

WT mice and ceramidase-deficient mice (Asah1$^{-/-}$) were infected intravenously with herpes simplex virus (HSV-1) ($7 \times 10^7$ PFU/mouse). After 4 hours, the propagation of the virus was measured in the liver by means of immunofluorescence. In this case, it was possible to demonstrate that ceramidase deficiency promotes the spreading of the virus in the liver of infected animals. The results obtained are depicted as immunofluorescence images in FIG. 7. Shown in white are HSV-1 in liver cells of infected wild-type (WT) animals and ceramidase-deficient (Asah1$^{-/-}$) animals (n=6).

2.8

Figure 8:
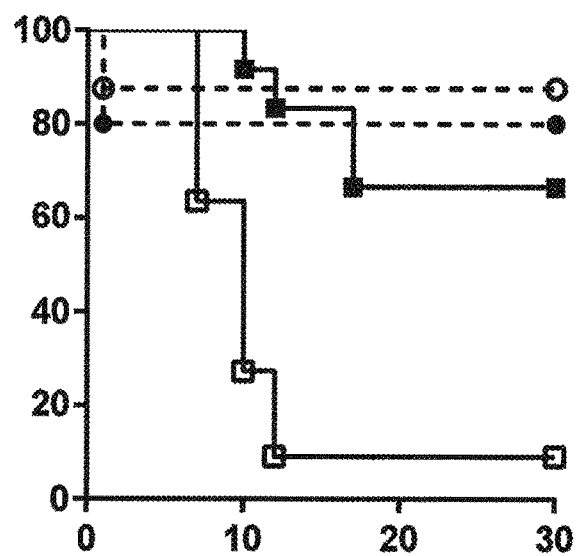
FIG. 8 illustrates survival of control mice and inducible ceramidase-deficient mice treated with tamoxifen in order to switch off the ceramidase demonstrating that ceramidase deficiency reduces the survival of the HSV-1 infected animals wherein Y-axis: Survival in percent; X-axis: Time after infection in days; and Treatment groups: Black squares: infected control animals; Black circles: uninfected control animals; White squares: infected ceramidase-deficient animals; White circles: uninfected ceramidase-deficient animals; p=0.0004.

Control mice and inducible ceramidase-deficient mice were treated with tamoxifen in order to switch off the ceramidase. The animals were left untreated or infected intravaginally with herpes simplex virus (HSV-1) ($2 \times 10^7$ PFU/mouse). The survival of the animals was ascertained. In this case, it was possible to demonstrate that ceramidase deficiency reduces the survival of the infected animals. The results obtained are depicted graphically in FIG. 8. p=0.0004; infected control animals (Cre$^-$ Asah1$^{fl/fl}$) n=12; infected ceramidase-deficient animals (Cre$^+$ Asah1$^{fl/fl}$) n=11; uninfected control animals (Cre$^-$ Asah1$^{fl/fl}$) n=5; uninfected ceramidase-deficient animals (Cre$^+$ Asah1$^{fl/fl}$) n=8.

2.9

Figure 9:
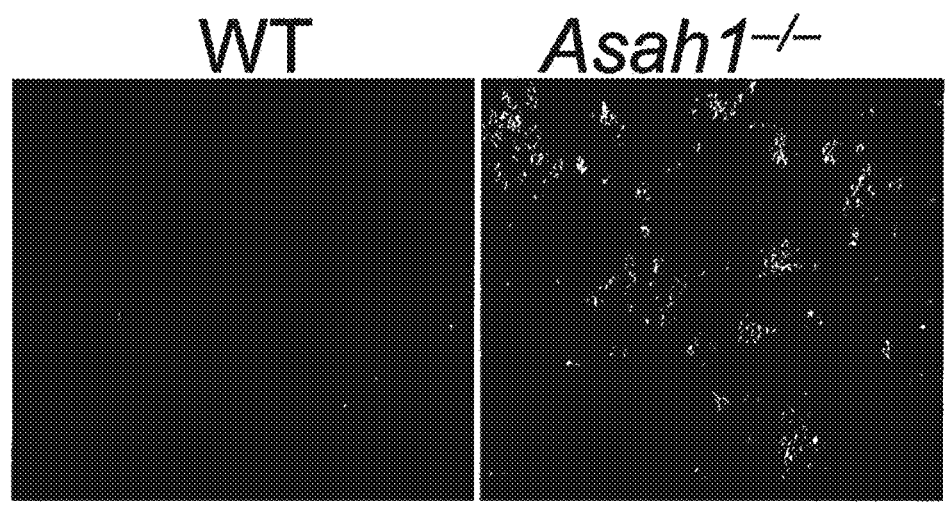
FIG. 9 illustrates propagation of LCMV in WT mice and ceramidase-deficient mice (Asah1$^{-/-}$) as measured in the liver demonstrating that ceramidase deficiency promotes the spreading of the virus in the liver of infected animals.

WT mice and ceramidase-deficient mice (Asah1$^{-/-}$) were infected intravenously with the lymphocytic choriomeningitis virus (LCMV) ($2 \times 10^6$ PFU/mouse). After 48 hours, the propagation of the virus was measured in the liver by means of immunofluorescence. In this case, it was possible to demonstrate that ceramidase deficiency promotes the spreading of the virus in the liver of infected animals. The results obtained are depicted as immunofluorescence images in FIG. 9. Shown in white are LCMV in liver cells from infected wild-type (WT) and ceramidase-deficient (Asah1$^{-/-}$) animals (n=6).

2.10

Figure 10:
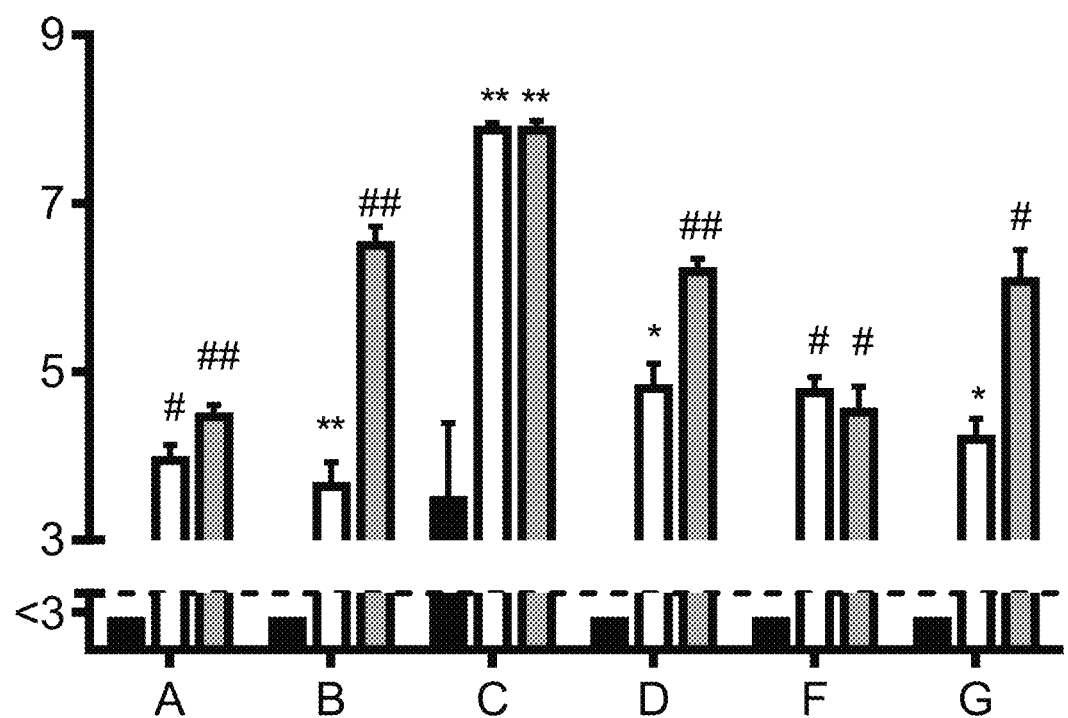
FIG. 10 illustrates propagation of lymphocytic choriomeningitis virus (LCMV) in WT mice (black bars), ceramidase-deficient mice (Asah1$^{-/-}$) (white bars) and interferon-alpha receptor-deficient mice (Ifnar$^{-/-}$) (gray bars) as measured in the blood (A), bone marrow (B), liver (C), lung (D), kidney (E), heart (F) and where Y-axis: Infectious LCMV particles in the organs measured (PFU/organ or PFU/ml of blood, logarithmic scale) demonstrating that ceramidase inhibits the propagation of LCMV in all the organs tested.

WT mice, ceramidase-deficient mice (Asah1$^{-/-}$) and interferon-alpha receptor-deficient mice (Ifnar$^{-/-}$) were infected intravenously with the lymphocytic choriomeningitis virus (LCMV) ($2 \times 10^6$ PFU/mouse). After 48 hours, the number of infectious virus particles was measured in different organs. In this case, it was possible to demonstrate that ceramidase inhibits the propagation of LCMV in all the organs tested. The inhibitory action of the ceramidase was just as strong as that of the strongest antiviral gene currently known, the type I interferon receptor (Ifnar). The results obtained are depicted graphically in FIG. 10. Shown is the mean±SEM, WT n=6; Asah1$^{-/-}$=4; Ifnar$^{-/-}$=4, *p<0.05; **p<0.01; # p<0.001; ## p<0.0001; student's T test.

2.11

Figure 11:
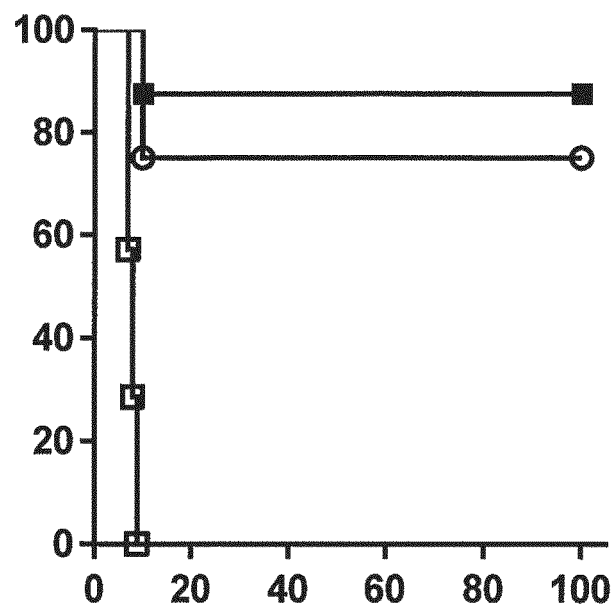
FIG. 11 illustrates survival of control mice and inducible ceramidase-deficient mice treated with tamoxifen in order to switch off the ceramidase demonstrating that ceramidase deficiency reduces the survival of the LCMV infected animals wherein Y-axis: Survival in percent; X-axis: Time after infection in days; and Treatment groups: Black squares: infected control animals; White squares: infected ceramidase-deficient animals; White circles: uninfected ceramidase-deficient animals; (p<0.0001).

Control mice and inducible ceramidase-deficient mice were treated with tamoxifen in order to switch off the ceramidase. The animals were left untreated or infected intravenously with the lymphocytic choriomeningitis virus (LCMV) ($2 \times 10^4$ PFU/mouse). In this case, it was possible to demonstrate that ceramidase deficiency reduces the survival of the infected animals. The results obtained are depicted graphically in FIG. 11. p<0.0001; infected control animals (Cre$^-$ Asah1$^{fl/fl}$) n=8; infected ceramidase-deficient animals (Cre$^+$ Asah1$^{fl/fl}$) n=7; uninfected ceramidase-deficient animals (Cre$^+$ Asah1$^{fl/fl}$) n=4.

2.12

Figure 12:
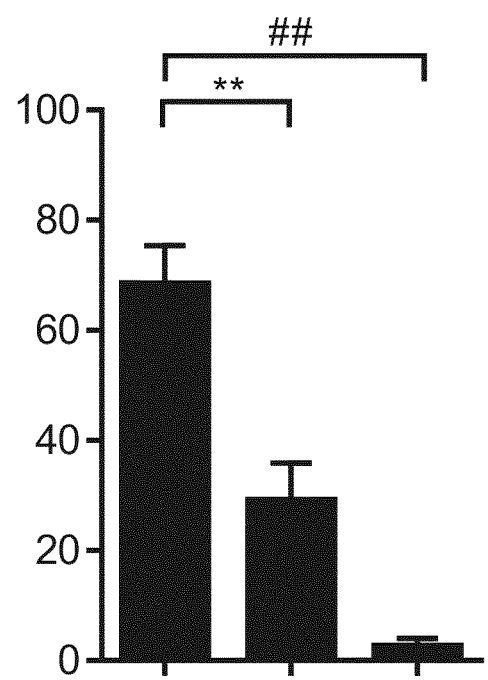
FIG. 12 illustrates Vero cells treated with 0, 10 and 50 mU/200 microliters (µl) ceramidase for 10 minutes and then infected with the vesicular stomatitis virus (VSV) demonstrating that the ceramidase inhibits the propagation of VSV where Y-axis: Number of resultant plaques per 24 wells and X-axis: Ceramidase concentration (mU/ml).

Confluently grown Vero cells were treated with 0, 10 and 50 mU/200 μl ceramidase for 10 minutes and then infected with the vesicular stomatitis virus (VSV) (100 PFU/well in a 24-well plate). After one hour, methylcellulose was added. After 24 hours, the number of plaques (due to holes in the cell lawn that are caused by the virus) was ascertained. In this case, it was possible to demonstrate that the ceramidase inhibits the propagation of VSV. The results obtained are depicted graphically in FIG. 12. Shown is the mean±SEM, 0 n=10, 10 n=8, 50 n=4, **p<0.01; ## p<0.0001; student's T test.

2.13

Figure 13:
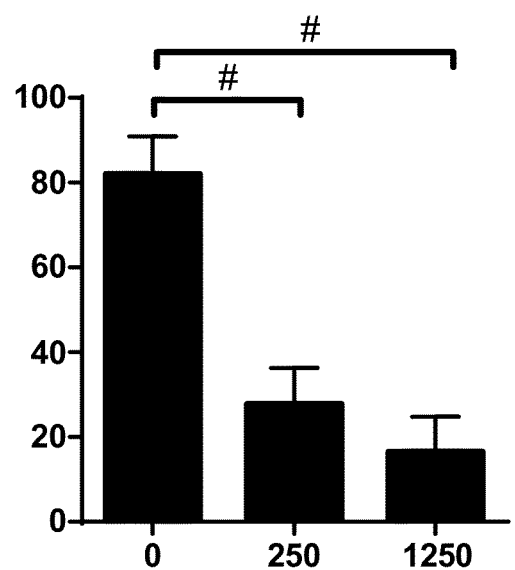
FIG. 13 illustrates Vero cells treated with 0, 250 and 1250 mU/ml sphingomyelinase for 10 minutes and then infected with the vesicular stomatitis virus (VSV) demonstrating that sphingomyelinase inhibits the propagation of VSV where Y-axis: Number of resultant plaques per 24 wells and X-axis: sphingomyelinase concentration (mU/200 µl).

Confluently grown Vero cells were treated with 0, 250 and 1250 mU/200 μl sphingomyelinase for 10 minutes and then infected with the vesicular stomatitis virus (VSV) (100 PFU/well in a 24-well plate). After one hour, methylcellulose was added. After 24 hours, the number of plaques (due to holes in the cell lawn that are caused by the virus) was ascertained. In this case, it was possible to demonstrate that the sphingomyelinase inhibits the propagation of VSV. The results obtained are depicted graphically in FIG. 13. Shown is the mean±SEM, 0 n=8, 250 n=8, 1250 n=4, # p<0.001, student's T test.

2.14

Figure 14:
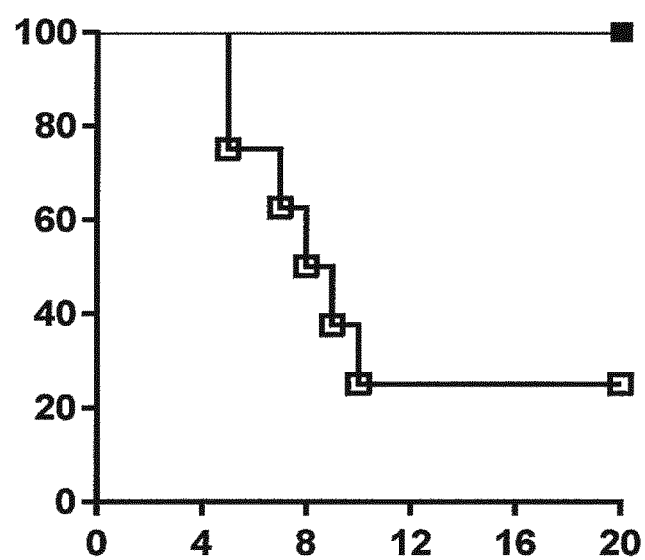
FIG. 14 illustrates survival of control mice and inducible ceramidase-deficient mice treated with tamoxifen in order to switch off the ceramidase. The animals were infected intravenously with the vesicular stomatitis virus (VSV) where the results demonstrate ceramidase deficiency reduces the survival of the infected animals and wherein Y-axis: Survival in percent; X-axis: Time after infection in days; and Treatment groups: Black squares: infected control animals; White squares: infected ceramidase-deficient animals; p=0.0041.

Control mice and inducible ceramidase-deficient mice were treated with tamoxifen in order to switch off the ceramidase. The animals were infected intravenously with the vesicular stomatitis virus (VSV) ($2 \times 10^6$ PFU/mouse). In this case, it was possible to demonstrate that ceramidase deficiency reduces the survival of the infected animals. The results obtained are depicted graphically in FIG. 14. p=0.0041; infected control animals (Cre$^-$ Asah1$^{fl/fl}$) n=7; infected ceramidase-deficient animals (Cre$^+$ Asah1$^{fl/fl}$) n=8.

2.15

Figure 15:
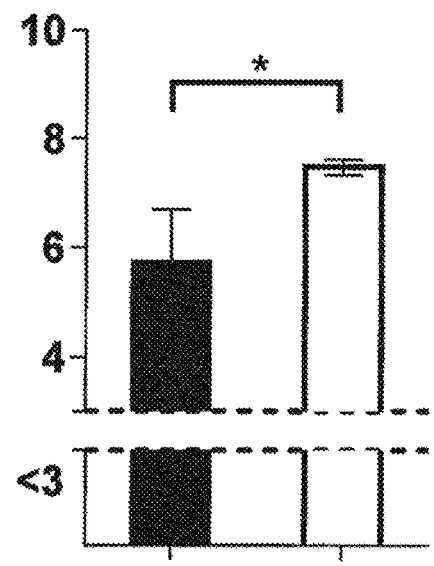
FIG. 15 illustrates the number of virus particles after 3 days in WT mice and ceramidase-deficient mice (Asah1$^{-/-}$) infected intranasally with the influenza A virus demonstrating that ceramidase prevents the propagation of IAV wherein Y-axis: Infectious IAV particles in the lung (PFU/lung, logarithmic scale) and Treatment groups: Black bars: infected control animals; White bars: infected ceramidase-deficient animals.

WT mice and ceramidase-deficient mice (Asah1$^{-/-}$) were infected intranasally with the influenza A virus (IAV) ($2.5 \times 10^5$ PFU/mouse). After 3 days, the number of infectious virus particles was measured in the lung. In this case, it was possible to demonstrate that ceramidase prevents the propagation of IAV. The results obtained are depicted graphically in FIG. 15. Shown is the mean±SD, WT n=8, Asah1$^{-/-}$ n=6, *p<0.05, student's T test.

2.16

Figure 16:
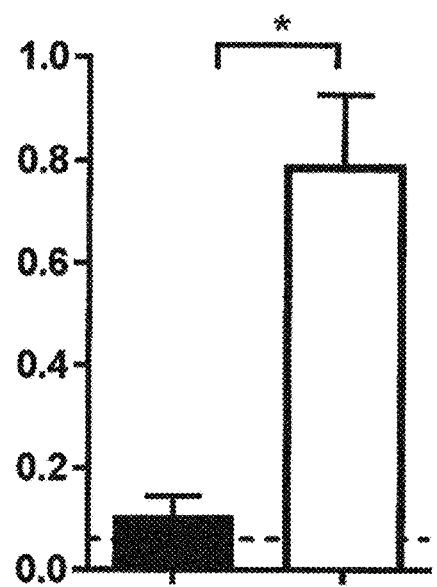
FIG. 16 illustrates percentage of infected erythroid progenitor cells after 6 days following infection of ceramidase-deficient mice (Asah1$^{-/-}$) were infected intravenously with the Friend virus (FV) demonstrating that ceramidase prevents the propagation of FV wherein Y-axis: Infected erythroid progenitor cells in percent and treatment groups: Black bars: infected control animals; White bars: infected ceramidase-deficient animals.

WT mice and ceramidase-deficient mice (Asah1$^{-/-}$) were infected intravenously with the Friend virus (FV) ($2\times10^4$ SFFU/mouse). After 6 days, the percentage of infected erythroid progenitor cells was measured. In this case, it was possible to demonstrate that ceramidase prevents the propagation of FV. The results obtained are depicted graphically in FIG. 16. Shown is the mean±SD, WT n=10, Asah1$^{-/-}$ n=6, *p<0.05, student's T test.

2.17

Figure 17:
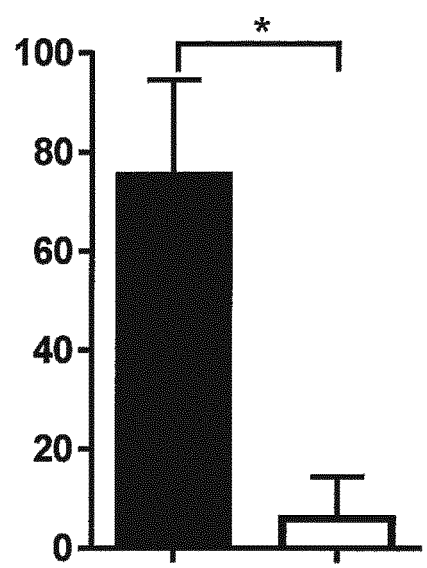
FIG. 17 illustrates propagation of HIV-P24 in human T cells as control or treated with 50 µM of the sphingosine kinase inhibitor MP A08 demonstrating that sphingosine kinase inhibition prevents the propagation of HIV wherein Y-axis: Amount of P24 (HIV antigen) in ng/ml and treatment groups: Black bars: untreated; White bars: inhibitor.

Human T cells were isolated from blood and infected with 63 ng/ml HIV-1 JR-CSF. One group was additionally treated with 50 µM of the sphingosine kinase inhibitor MP A08. After 7 days, the amount of HIV-P24 in the supernatant of the cultures was quantified by means of ELISA. In this case, it was possible to demonstrate that sphingosine kinase inhibition prevents the propagation of HIV. The results obtained are depicted graphically in FIG. 17. Shown is the mean±SEM, n=9, *p<0.05, student's T test.

2.18

Figure 18:
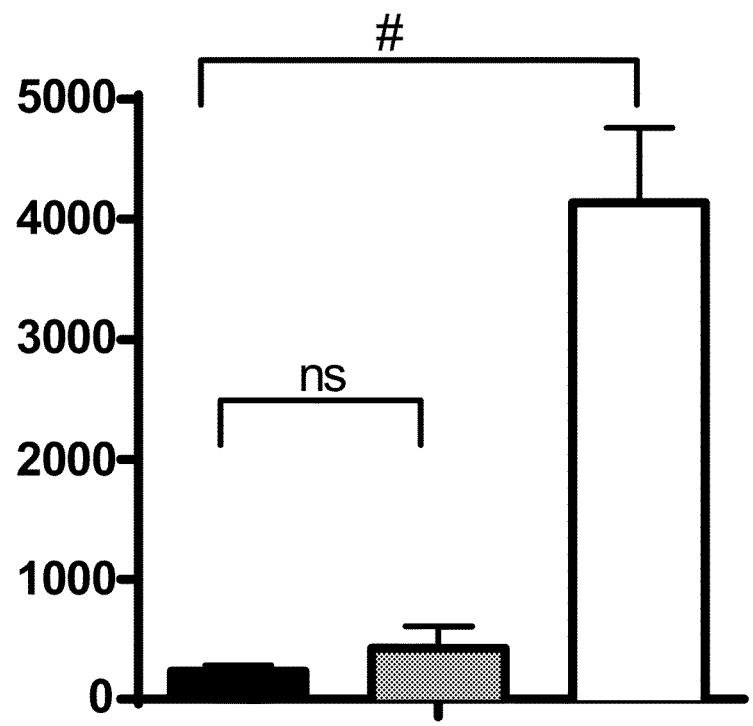
FIG. 18 illustrates binding of lymphocytic choriomeningitis virus to control liposomes, and liposomes enriched with ceramide or sphingosine demonstrating that sphingosine-containing liposomes can bind a virus rapidly wherein Y-axis: Virus binding (mean fluorescence intensity) and Treatment groups: Black bars: control liposomes; Grey bars: ceramide liposomes; White bars: sphingosine liposomes.

Liposomes were enriched by means of ceramide or sphingosine. Control liposomes, ceramide liposomes and sphingosine liposomes were incubated with fluorescent lymphocytic choriomeningitis virus (LCMV). After 10 minutes, the binding of the virus was measured using a flow cytometer. In this case, it was possible to demonstrate that sphingosine-containing liposomes can bind a virus rapidly. The results obtained are depicted graphically in FIG. 18. Shown is the mean±SD, n=3, ns—not significant, # p<0.001, student's T test.

2.19

Figure 19:
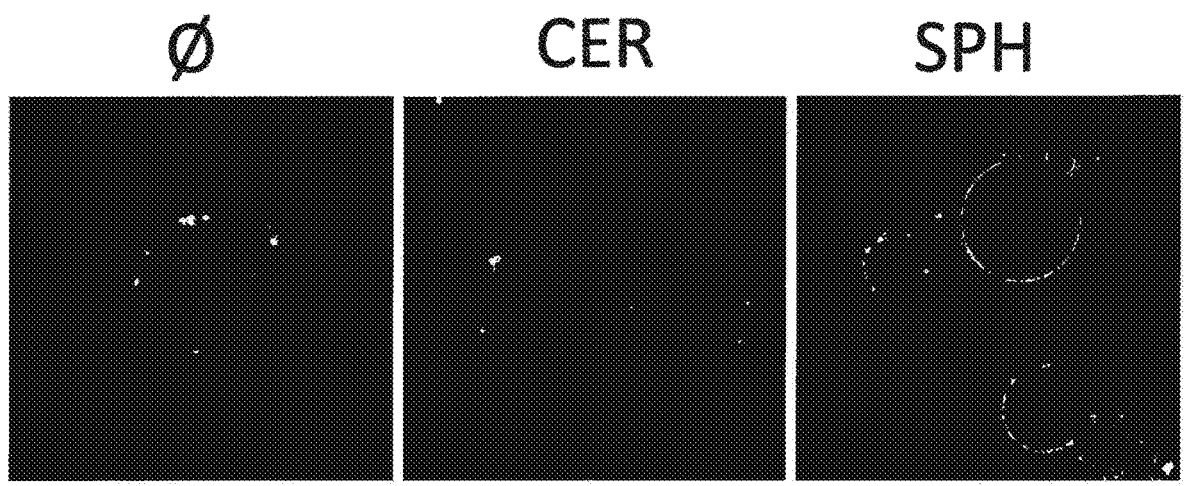
FIG. 19 illustrates micrographs of the liposomes of FIG. 18 wherein white are LCMV binding to the liposomes. ø: control liposomes; CER: ceramide liposomes; SPH: sphingosine liposomes.

Liposomes were enriched by means of ceramide or sphingosine. Control liposomes, ceramide liposomes and sphingosine liposomes were incubated with the fluorescent lymphocytic choriomeningitis virus (LCMV). After 10 minutes, the binding of the virus was measured by means of confocal microscopy. In this case, it was possible to demonstrate that sphingosine-containing liposomes can bind a virus rapidly. The results obtained are depicted as micrographs in FIG. 19 (n=3).

3. The Effect of Sphingosine on Rhinoviral (RV) Infections 3.1

Sphingosine was added to human epithelial Hela cells at different concentrations and different times prior or after viral infections. Hela cells were cultured in 24 well plates in DMEM supplemented with 2 mM L-glutamine, 1 mM sodium pyruvate, 100 µM nonessential amino acids, 100 U/mL penicillin, 100 µg/mL streptomycin (all from Invitrogen) and 10% fetal calf serum (PAA Laboratories GmbH, Coelbe, Germany) and grown until they reached approximately 70% density. Cells were washed twice in DMEM supplemented with 2% FCS and recultured in DMEM/2% FCS. $5\times10^5$ Hela cells were infected with $10^5$ PFU of rhinovirus strains RV2 (minor strain) or RV14 (major strain). Rhinoviruses were obtained from ATCC. Sphingosine was added at 10 µM or 20 µM final concentration 10 min prior the infection (before infection, b.i.) with rhinoviruses or 60 min or 240 min after infection (a.i.) with rhinoviruses. Sphingosine was diluted from a 20 mM stock in 10% octylglucopyranoside (OGP) in distilled water. Thus, controls were 0.005% or 0.01% OGP final concentrations. Further controls were infected, but not further treated. The samples were incubated for 4 hrs at 33° C. after initiating the infection, the supernatant was removed, DMEM/10% FCS was added and the cells were incubated for an additional 4 days. Cell death was determined as a measurement for the infection by staining the cells with Trypan Blue. Rhinoviruses are cytotoxic and the number of dead cells accurately reflects the rhinoviral infection. We determined the percentage of dead cells by counting 500 cells/sample using a cell culture microscopy.

Figure 20:
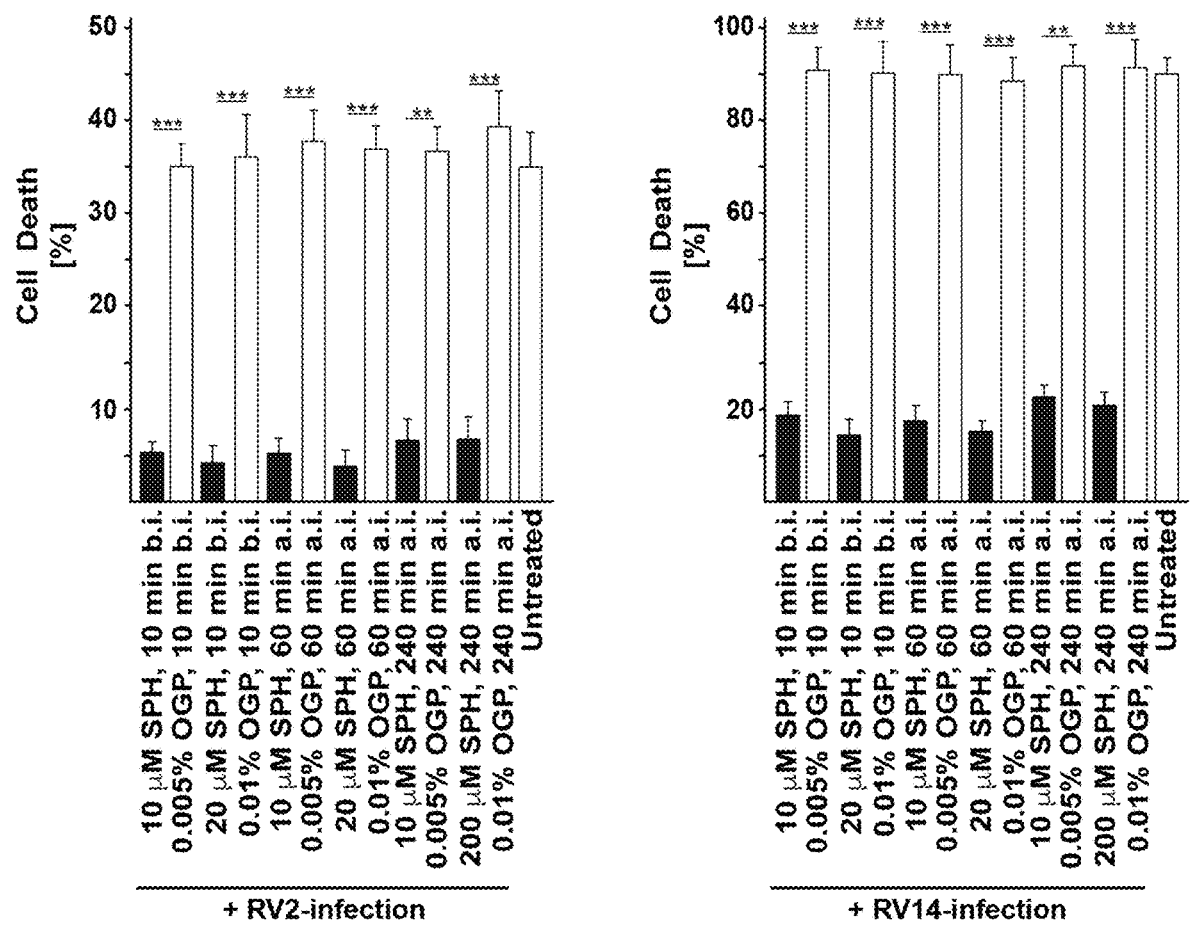
FIG. 20 illustrates the prevention of RSV2 and RSV14 infection in Hela cells treated with sphingosine relative to control and independent of whether sphingosine was added prior to or following infection.

As illustrated in FIG. 20 sphingosine prevented the infection with RV2 and RV14 at 10 µM and 20 µM. An increase of the sphingosine concentration to 20 µM did not significantly increase the inhibition of viral infections by sphingosine. Sphingosine prevented the infection if added prior to the virus or after infection with the virus up to 4 hrs. Sphingosine itself had no effect on the cells. OGP did not alter the infection. Shown is the percentage of dead cells 4 days after initiating the infection ±SD, n=5 each, ***p<0.001, ANOVA.

3.2

Sphingosine (SPH) was applied into the nose of wild-type mice and the concentration of sphingosine on the epithelial cell surface was determined after 1, 4 and 8 hrs (a.i.: after injection of sphingosine). To this end, 10 µL of a 10 µM or a 100 µM sphingosine solution was applied into the nostrils of wild-type mice. Controls received the solvent, i.e. octylglucopyranoside at the same concentration used when sphingosine was applied, or were left untreated. Mice were slightly and very briefly anesthetized with ether. For the intranasal application we used a blunt-end 30 g needle that was covered with a thin plastic film. The blunt-ended needle was inserted into the nostrils approximately 2 mm. Mice were sacrificed after the indicated time, the nasal bone was removed, placed on a 30° C. pre-warmed plastic plate and an area of 2 mm×2 mm was immediately incubated with 0.001 units of sphingosine kinase 1 (#6068-SK-010, R&D) in 4 µl of 150 mM sodium acetate (pH 7.4), 1 µM ATP, and 10 µCi [$^{32}$P]γATP/sample. Controls were incubated with the same buffer without sphingosine kinase or were left untreated. The sphingosine kinase reaction was terminated by adding 100 µl $H_2O$, followed by the addition of 20 µl N HCl, 800 µl $CHCl_3$:$CH_3OH$:1N HCl (100:200:1, v:v:v), and 240 µl each of $CHCl_3$ and 2 M KCl. The lower phase was collected, dried, dissolved in 20 µL $CHCl_3$:$CH_3OH$ (1:1, v/v), and separated on Silica G60 TLC plates with $CHCl_3$:$CH_3OH$: acetic acid:$H_2O$ (90:90:15:5, v:v:v:v) as a developing solvent. The TLC plates were analyzed with a phosphoimager. Surface sphingosine levels were determined with a standard curve of C18-sphingosine.

The assays were performed without washing the mucosa on the nasal bone, i.e. immediately after removal, and, in addition, after extensive washing the specimen in PBS to remove mucus from the epithelial cell surface.

Figure 21:
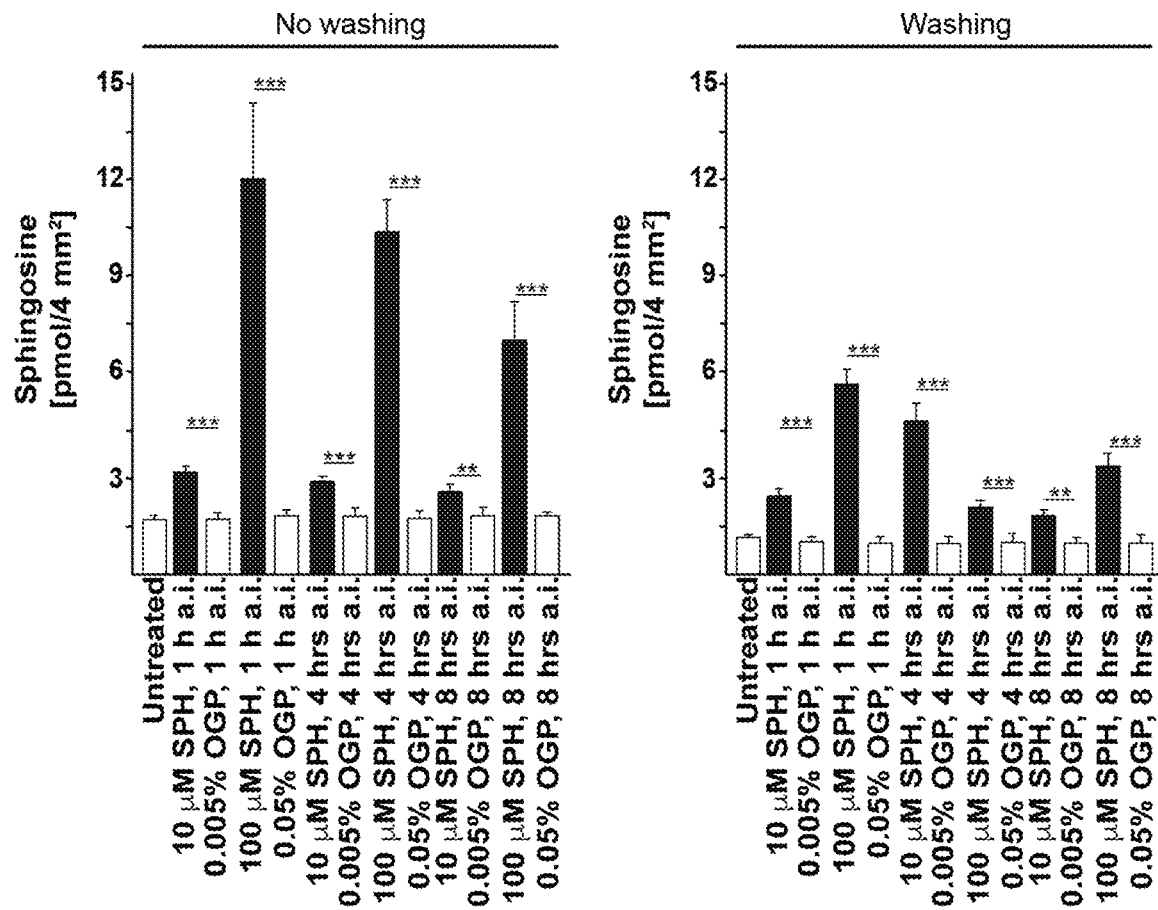
FIG. 21 illustrates that application of sphingosine to the nose of mice results in a dose dependent increase in the local sphingosine concentration in the nasal mucosa and that this increase was not appreciably removed by washing.
Figure 22:
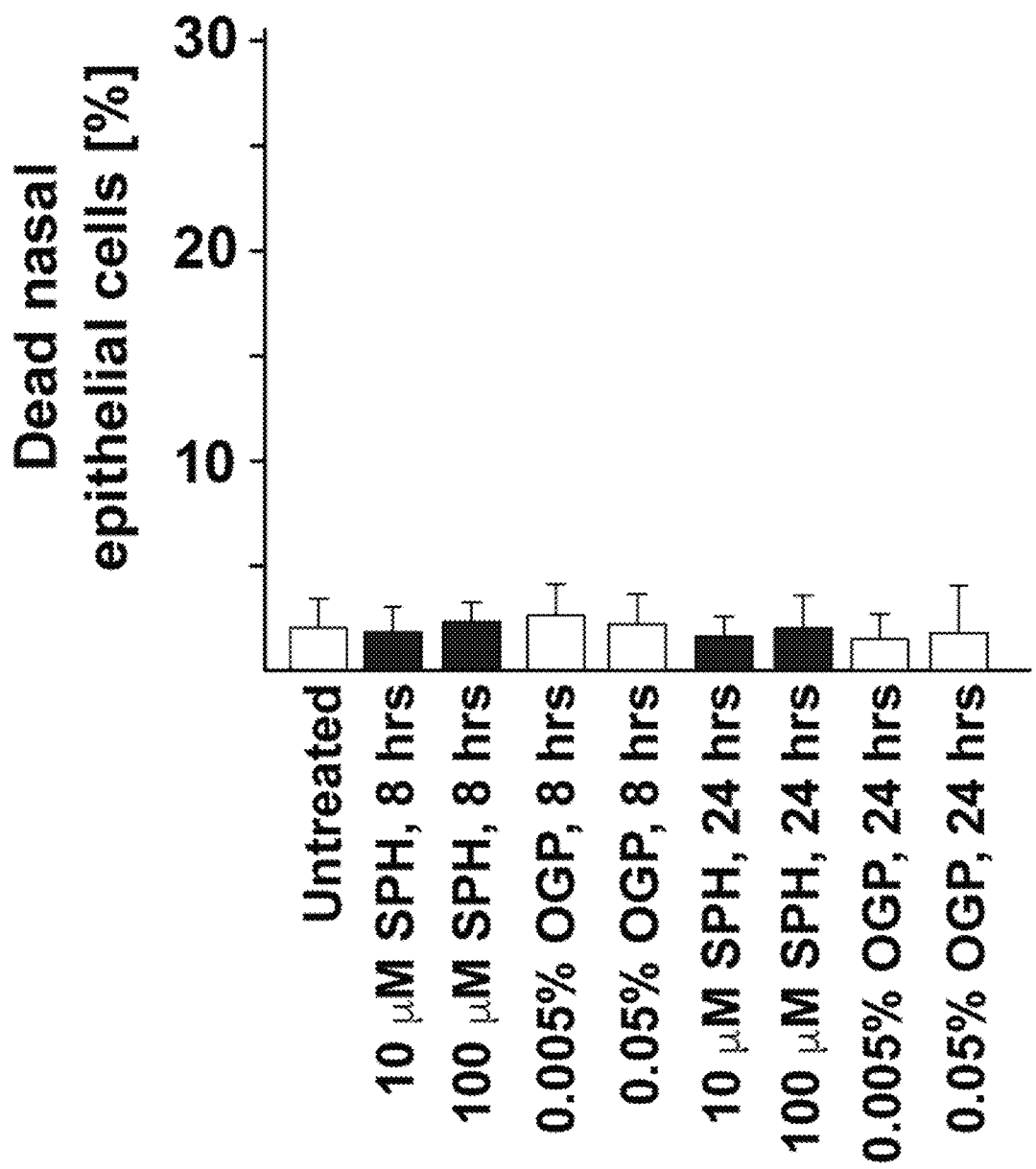
FIG. 22 illustrates application of sphingosine into the nose of mice results in no toxic side effects.

The results are depicted in FIG. 21 illustrating that application of sphingosine into the nose of wild-type mice results in a dose-dependent accumulation of sphingosine in the mucosa. Washing the mucosa prior to the in situ kinase assay reduces sphingosine accumulation in the nasal specimen on top of the epithelial cell layer indicating that most sphingosine remains in the mucus on top of the epithelial cell layer. Shown are the surface concentration, mean±SD, n=4, ***p<0.001, ANOVA.

3.3

Sphingosine was applied into the nose of wild-type mice as in 3.2. 10 µL of a 10 µM or a 100 µM sphingosine (SPH) solution was administered into the nostrils of wild-type mice. Controls received the solvent, i.e. octylglucopyranoside at the same concentration used when sphingosine was applied, or were left untreated. Mice were anesthetized prior to application of sphingosine. Mice were sacrificed after 8 hours or 24 hours, the nasal bone was removed and incubated in Trypsin solution for 10 min to release and isolate epithelial cells. Cells were washed twice in H/S (20 mM HEPES, 132 mM NaCl, 5 mM KCl, 1 mM $CaCl_2$, 0.7 mM $MgCl_2$, 0.8 mM $MgSO_4$, pH 7.4), stained with Trypan Blue (0.2% final concentration) and dead cells were counted in aliquots of 500 cells. Given is the percentage of dead cells ±SD from 4 independent experiments each; *p<0.05, ANOVA. The results show that sphingosine at the applied doses had no toxic effects on epithelial cells of the nose.

3.4

Figure 23:
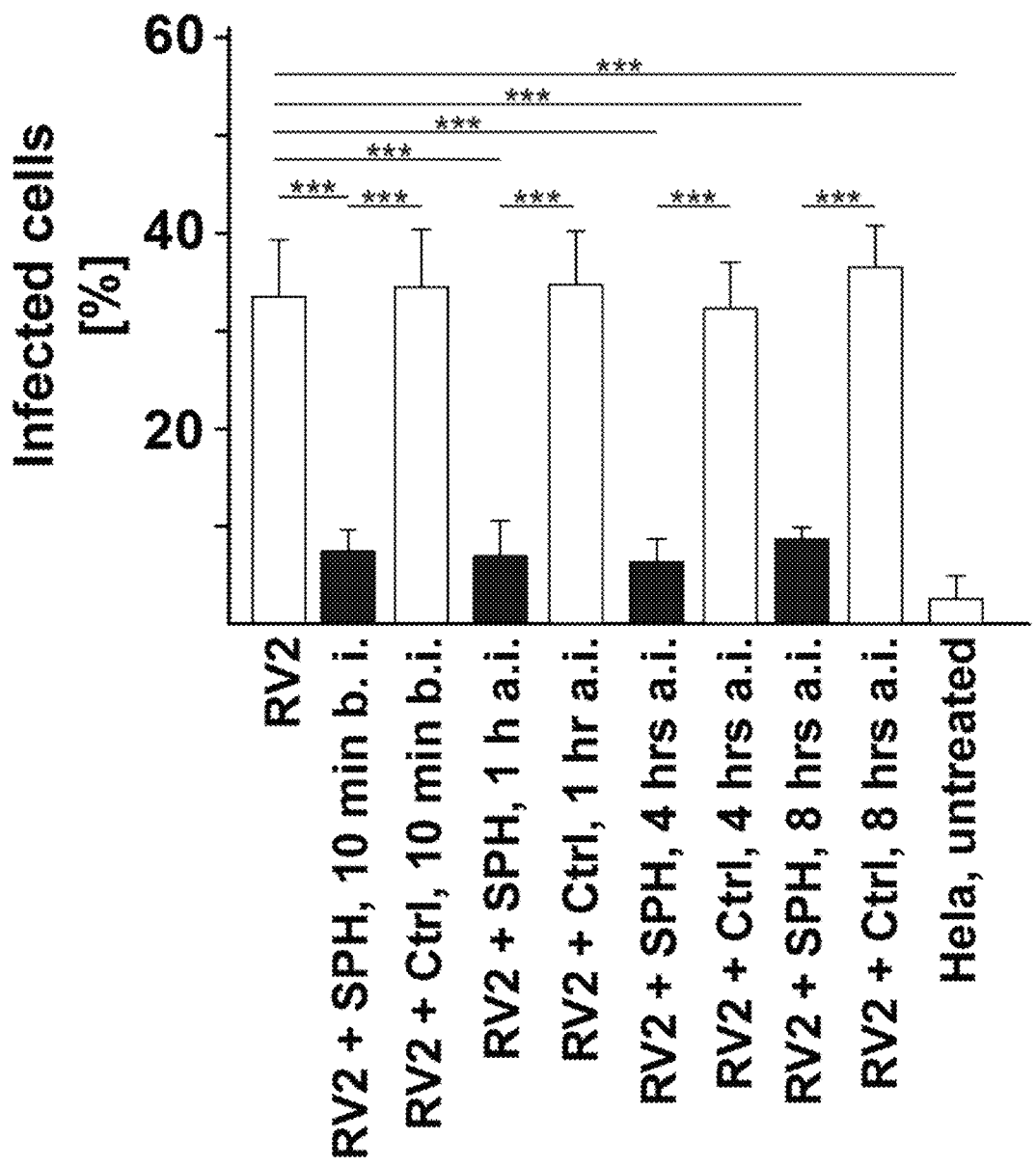
FIG. 23 illustrates that administration of prophylactic or post-infection nasal administration of sphingosine to wild-type mice prevents infection by RSV2.

Mice were infected with $10^3$ PFU rhinovirus strain 2 (RV2) in 10 µL PBS. The virus was applied directly into the nose using a blunt ended, plastic coated 30 g needle, that was inserted into the nose approximately 2 mm. Sphingosine (SPH) was applied into the nose of the wild-type mice at a concentration of 100 µM solution in PBS in a volume of 10 µL. Sphingosine was applied either 10 min prior to rhinovirus infection (b.i.) or 1 hr, 4 hrs and 8 hrs after the infection (a.i.). Controls received the solvent, i.e. octylglucopyranoside (OGP) at the same concentration than used when sphingosine was applied, or were left untreated, but infected. Solutions were applied as in 3.2. Mice were sacrificed after 24 hrs, the nasal bone was removed and incubated for 4 days with Hela cells in a 24 well plate. If the nasal epithelial cells are infected, rhinovirus will be released due to the cytopathic effect of the virus and the in vivo infection can then be determined and quantified by measuring cell death of Hela cells as a bioassay. To this end, dead cells were collected, adherent cells were trypsinized, the fractions were combined, washed twice in H/S (20 mM HEPES, 132 mM NaCl, 5 mM KCl, 1 mM $CaCl_2$), 0.7 mM $MgCl_2$, 0.8 mM $MgSO_4$, pH 7.4), stained with Trypan Blue (0.2% final concentration) and dead cells were counted in aliquots of 500 cells as above. Results are illustrated in FIG. 23 and given as the percentage of dead cells ±SD from 4 independent experiments each; *p<0.05, ANOVA.

The results show that intranasal application of RV2 into wild-type mice resulted in an infection with RV2, which was prevented by prophylactic application of sphingosine or by application of sphingosine 1, 4 or 8 hrs after the infection. OGP was without effect on the infection.

3.5

Figure 24:
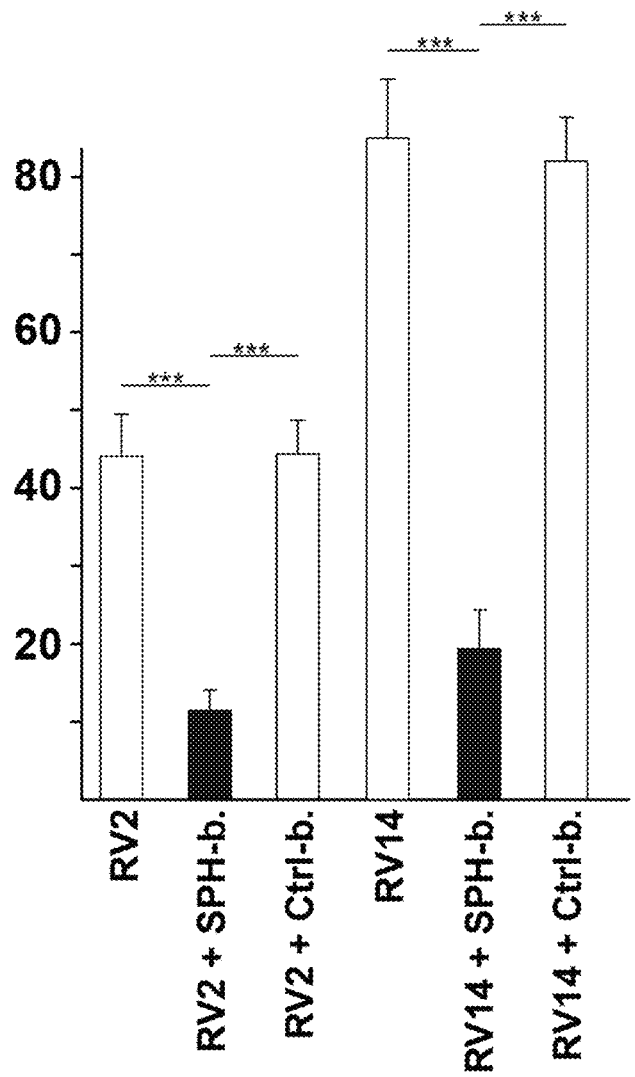
FIG. 24 illustrates that sphingosine-coupled agarose beads efficiently bind RV2 or RV14 wherein the Y-axis is the percentage of dead Hela cells following incubation with the supernatant of sphingosine-coupled agarose beads with virus.
Figure 25:
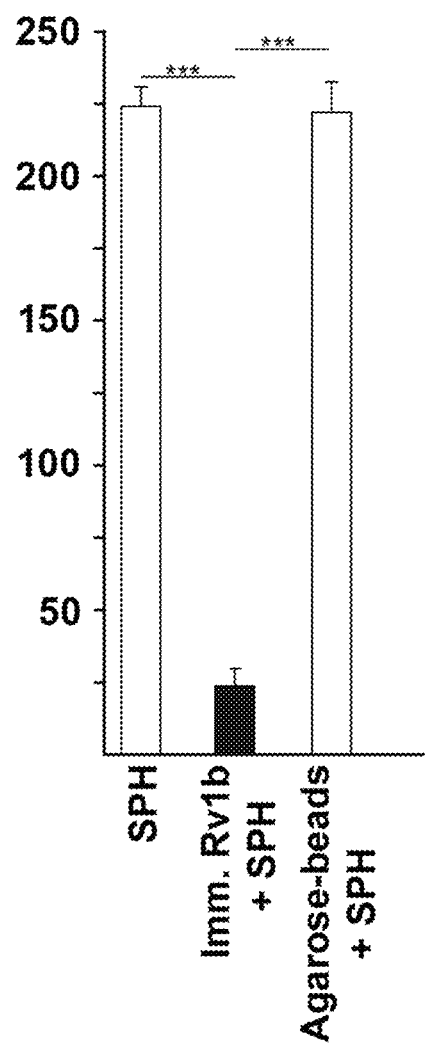
FIG. 25 illustrates that RV1b-coupled agarose beads efficiently bind sphingosine wherein the Y-axis is the remaining sphingosine in the supernatant in 04.

Sphingosine (SPH) that was immobilized to agarose beads (Echelon Biosciences), or control beads (Ctrl) were incubated with $10^4$ PFU of rhinovirus 2 or 14 (RV2 or RV14) for 4 hrs at 4° C. in a volume of 400 µL PBS. The beads were then centrifuged for 2 min at 14 000 rpm in a centrifuge, the supernatant was completely removed. The supernatant was then incubated for 4 days with Hela cells in 24 well plates (grown to 70% confluency) to determine the remaining viral titer in the supernatant and, thus, to determine binding of the virus to sphingosine and thereby depletion of the virus from the supernatant. The supernatant was added to Hela cells and as readout for remaining virus the number of dead Hela cells in aliquots of 500 cells after 4 days of culture was determined. FIG. 24 illustrates the percentage of dead cells ±SD from 5 independent experiments each; *p<0.05, ANOVA. The results show that sphingosine-coupled agarose beads efficiently bound RV2 or RV14 and almost completely depleted the supernatant from any virus.

As a complement to the above study, RV1b (obtained from ATCC) were immobilized to agarose beads and tested for binding of sphingosine (SPH). To this end, we incubated 1 µg/ml anti-RV1b antibodies with $10^6$ CFU RV1b for 1 h at 4° C. in H/S, added 50 µL agarose protein A/G beads (Santa Cruz Inc.), incubated for an additional 1 h at 4° C. and washed the immobilized precipitates 5-times in H/S. We resuspended the beads in 500 µL PBS (pH 7.0) containing 250 µM sphingosine. Samples were incubated for 4 hrs at 4° C., pelleted and aliquots of the supernatants were added to 50 mM HEPES (pH 7.4), 250 mM NaCl, 30 mM $MgCl_2$, 0.001 units sphingosine kinase (R&D), 1 mM ATP and 10 µCi [$^{32}$P]γATP. The kinase reaction was performed for 1 hr at 30° C., stopped by addition of 20 µl N HCl, 800 µl $CHCl_3/CH_3OH/1N$ HCl (100:200:1, v/v/v), 240 µl $CHCl_3$ and 2 M KCl. Phases were separated, the lower phase was collected, dried, dissolved in 20 µL of $CHCl_3:CH_3OH$ (1:1, v/v) and separated on Silica G60 thin layer chromatography (TLC) plates using $CHCl_3/CH_3OH$/acetic acid/$H_2O$ (90:90:15:5, v/v/v/v). The TLC plates were exposed to radiography films, spots were removed from the plates, and the incorporation of [$^{32}$P] into sphingosine measured by liquid scintillation counting. Sphingosine was determined using a standard curve of C18-SPH. Given is the mean of the remaining sphingosine concentration in the supernatant ±SD from 5 independent experiments each; ***p<0.001, ANOVA.

Figure 26:
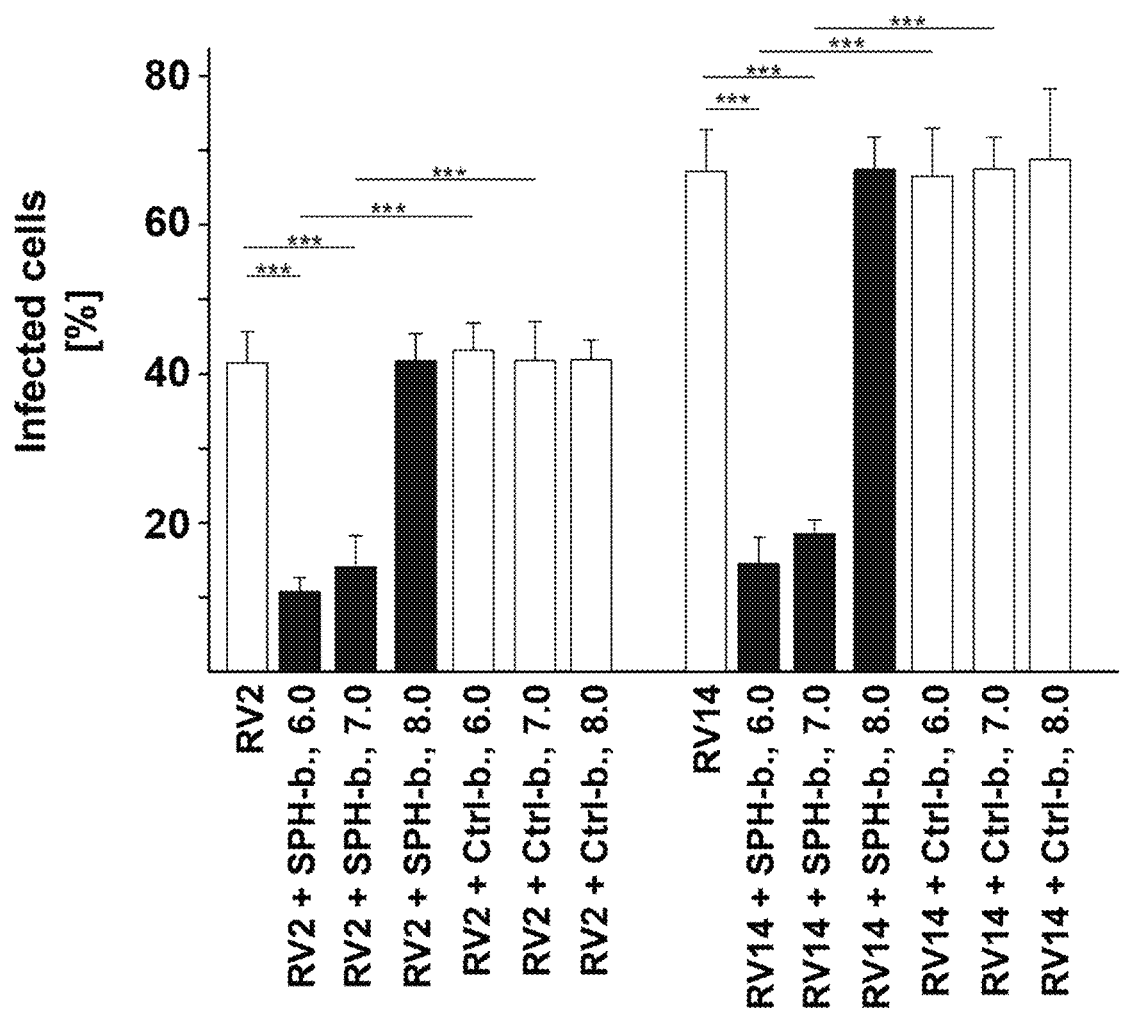
FIG. 26 illustrates pH affects on the binding of sphingosine to RV2 or RV14.

To test whether binding of sphingosine (SPH) to RV2 or RV14 depends on the pH and, thus, presumably on protonation of the $NH_2$ group in sphingosine, sphingosine-agarose beads or control (Ctrl) beads were incubated with $10^4$ PFU RV2 or RV14 for 4 hrs at 4° C. in a volume of 400 µL 150 mM sodium acetate adjusted to pH 6.0, pH 7.0 or pH 8.0. Studies where then performed as in the preceding two paragraphs and determined the number of virus in the supernatant by a bioassay using the cytopathic effect of the virus on Hela cells as readout. Given is the mean of the percentage of dead Hela cells ±SD from 5 independent experiments each; *p<0.001, ANOVA. The results as illustrated in FIG. 26** demonstrate that sphingosine-coupled agarose beads bind virus and, thus, deplete the supernatant from virus at pH 6.0 and pH 7.0, while binding of sphingosine to RV2 or RV14 is abrogated at pH 8.0. This suggests that protonation of the $NH_2$ group in sphingosine determines direct binding of sphingosine to the viruses. Control beads did not bind rhinovirus.

3.6

Figure 27:
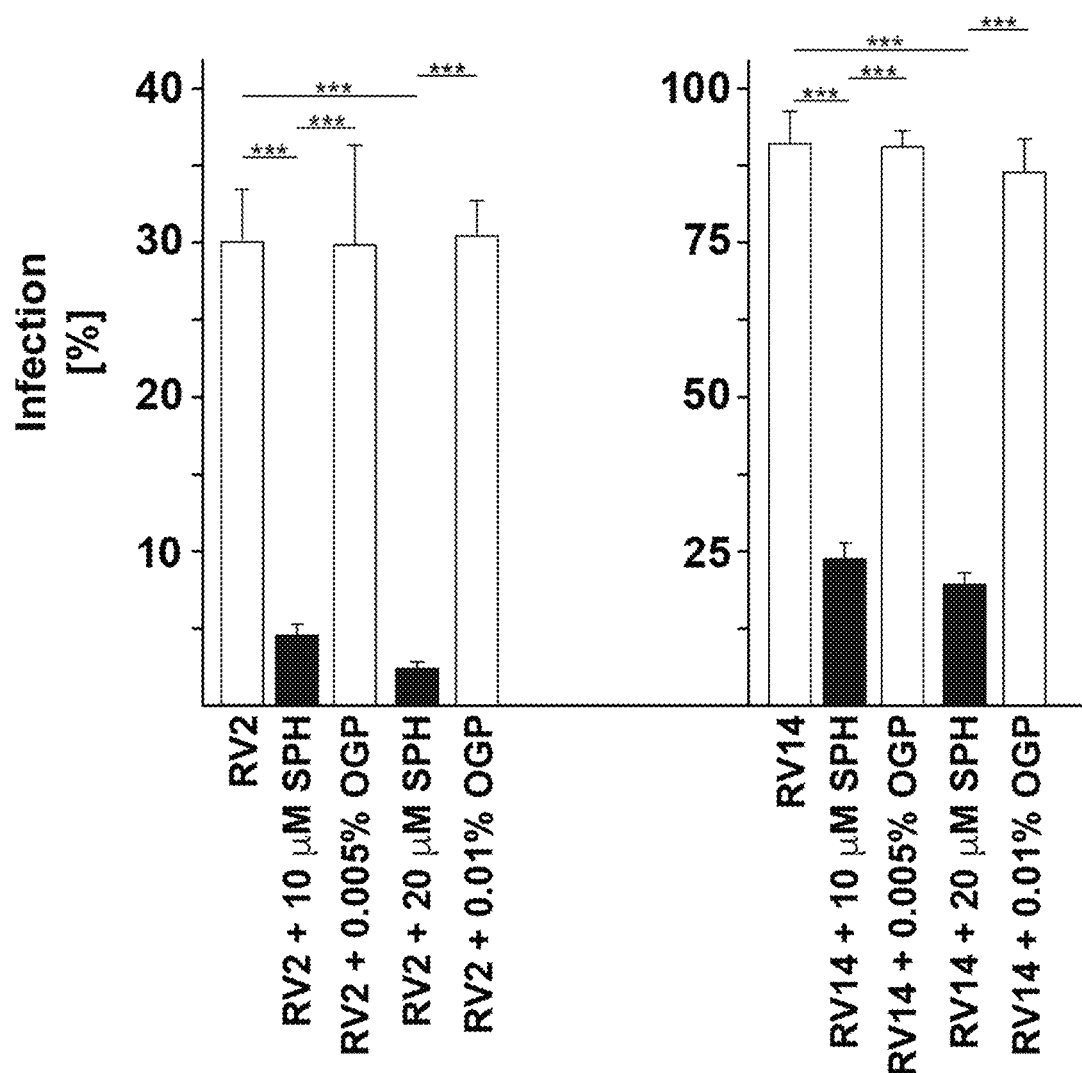
FIG. 27 illustrates that sphingosine prevents infection of freshly isolated human nasal epithelial cells by both RV2 and RV14.

$10^4$ PFU of Rhinovirus 2 or 14 (RV2, RV14) were incubated with freshly isolated human epithelial cells for 24 hrs in the presence of 10 µM or 20 µM sphingosine (SPH) or the corresponding concentration of the solvent octylglucopyranoside (OGP), the cells were pelleted, supernatants completely removed, the cell pellets resuspended in PBS and added to Hela cells. Cells were incubated for 3 days and cytotoxicity as measurement for virus titers was determined. Shown is the mean±SD, n=4, *p<0.001 ANOVA. As shown in FIG. 27, the presence of sphingosine abrogates infection of human epithelial cells by both RV2 and RV14.

The foregoing description of particular aspect(s) is merely exemplary in nature and is in no way intended to limit the scope of the invention, its application, or uses, which may, of course, vary. The invention is described with relation to the non-limiting definitions and terminology included herein. These definitions and terminology are not designed to function as a limitation on the scope or practice of the invention but are presented for illustrative and descriptive purposes only. While the processes or compositions are described as an order of individual steps or using specific materials, it is appreciated that steps or materials may be interchangeable such that the description of the invention may include multiple parts or steps arranged in many ways as is readily appreciated by one of skill in the art.

It will be understood that, although the terms "first," "second," "third" etc. may be used herein to describe various elements, components, regions, layers, and/or sections, these elements, components, regions, layers, and/or sections should not be limited by these terms. These terms are only used to distinguish one element, component, region, layer, or section from another element, component, region, layer, or section. Thus, "a first element," "component," "region," "layer," or "section" discussed below could be termed a second (or other) element, component, region, layer, or section without departing from the teachings herein.

The terminology used herein is for the purpose of describing particular embodiments only and is not intended to be limiting. As used herein, the singular forms "a," "an," and "the" are intended to include the plural forms, including "at least one," unless the content clearly indicates otherwise. "Or" means "and/or." As used herein, the term "and/or" includes any and all combinations of one or more of the associated listed items. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof. The term "or a combination thereof" means a combination including at least one of the foregoing elements.

Unless otherwise defined, all terms (including technical and scientific terms) used herein have the same meaning as commonly understood by one of ordinary skill in the art to which this disclosure belongs. It will be further understood that terms such as those defined in commonly used dictionaries, should be interpreted as having a meaning that is consistent with their meaning in the context of the relevant art and the present disclosure, and will not be interpreted in an idealized or overly formal sense unless expressly so defined herein.

Various modifications of the present invention, in addition to those shown and described herein, will be apparent to those skilled in the art of the above description. Such modifications are also intended to fall within the scope of the appended claims.

It is appreciated that all reagents are obtainable by sources known in the art unless otherwise specified.

Patents, publications, and applications mentioned in the specification are indicative of the levels of those skilled in the art to which the invention pertains. These patents, publications, and applications are incorporated herein by reference to the same extent as if each individual patent, publication, or application was specifically and individually incorporated herein by reference.

The foregoing description is illustrative of particular aspects of the invention, but is not meant to be a limitation upon the practice thereof. The following claims, including all equivalents thereof, are intended to define the scope of the invention.

The invention claimed is:

1. A process of treating or preventing a viral infection in a subject comprising:
    administering to a subject in need of prevention or treatment of a rhinovirus infection a composition comprising sphingosine;
    wherein administration is nasally or intravenously; and
    thereby treating or preventing infection by a rhinovirus in the subject by reducing the amount of infective virus in the subject through the action of said sphingosine.

2. The process of claim 1 wherein the administration is of the compound or active ingredient is from 0.001 mg/kg body weight to 10 mg/kg body weight of the subject.

3. The process of claim 1 wherein the virus is a rhinovirus, the subject is a human, the administration is nasally, and the composition comprises sphingosine.

* * * * *